US012580065B2

(12) United States Patent
Hebert et al.

(10) Patent No.: US 12,580,065 B2
(45) Date of Patent: Mar. 17, 2026

(54) IMAGE QUALITY RELATIVE TO MACHINE LEARNING DATA

(71) Applicant: Elekta Limited, Montreal (CA)

(72) Inventors: Francois Hebert, Montréal (CA); Sebastien Tremblay, Saint-Jean-sur-Richelieu (CA)

(73) Assignee: Elekta Limited, Montreal (CA)

( * ) Notice: Subject to any disclaimer, the term of this patent is extended or adjusted under 35 U.S.C. 154(b) by 285 days.

(21) Appl. No.: 18/568,000

(22) PCT Filed: Jun. 17, 2021

(86) PCT No.: PCT/CA2021/050824
§ 371 (c)(1),
(2) Date: Dec. 7, 2023

(87) PCT Pub. No.: WO2022/261742
PCT Pub. Date: Dec. 22, 2022

(65) Prior Publication Data
US 2024/0242813 A1    Jul. 18, 2024

(51) Int. Cl.
*G16H 20/40* (2018.01)
*G06T 7/00* (2017.01)
(Continued)

(52) U.S. Cl.
CPC ........... *G16H 20/40* (2018.01); *G06T 7/0012* (2013.01); *G06V 10/761* (2022.01); *G16H 30/40* (2018.01);
(Continued)

(58) Field of Classification Search
CPC ......... G06T 7/0012; G06T 2207/10072; G06T 2207/20081; G06T 2207/20084;
(Continued)

(56) References Cited

U.S. PATENT DOCUMENTS

| | | | |
|---|---|---|---|
| 10,867,417 B2 | 12/2020 | Han | |
| 2010/0189320 A1* | 7/2010 | Dewaele | G06T 7/11 |
| | | | 382/128 |

(Continued)

FOREIGN PATENT DOCUMENTS

| | | |
|---|---|---|
| WO | WO-2021026634 A1 | 2/2021 |
| WO | WO-2022261742 A1 | 12/2022 |
| WO | WO-2023279188 A1 | 1/2023 |

OTHER PUBLICATIONS

"International Application Serial No. PCT/CA2021/050824, International Search Report mailed Mar. 16, 2022", 3 pgs.
"International Application Serial No. PCT/CA2021/050824, Written Opinion mailed Mar. 16, 2022", 5 pgs.
(Continued)

*Primary Examiner* — Andrew M Moyer
(74) *Attorney, Agent, or Firm* — Schwegman Lundberg & Woessner, P.A.

(57) ABSTRACT

Systems and methods are disclosed for performing operations comprising: receiving a plurality of training medical images used to train a machine learning technique; applying a model to the plurality of training medical images to generate a distribution representation of the plurality of training medical images; computing a first distance between a given training medical image in the plurality of training medical images and the distribution representation; computing a second distance between a new medical image and the distribution representation; and computing a quality factor indicating a measure of similarity between a new medical image and the plurality of medical images as a function of the first distance and the second distance.

27 Claims, 11 Drawing Sheets

(51) Int. Cl.
    *G06V 10/74*      (2022.01)
    *G16H 30/40*     (2018.01)

(52) U.S. Cl.
    CPC ............... *G06T 2207/10072* (2013.01); *G06T 2207/20081* (2013.01); *G06T 2207/20084* (2013.01); *G06T 2207/30096* (2013.01); *G06V 2201/032* (2022.01)

(58) Field of Classification Search
    CPC ........ G06T 2207/30096; G06V 10/761; G06V 2201/032; G16H 30/40; G06N 3/047; G06N 3/0475; G06N 3/0455; G06N 3/0464; G06N 3/084; G06N 20/00; A61B 6/032; A61B 6/4085; A61B 6/5264; A61N 2005/1055; A61N 5/1049; G01R 33/4808
See application file for complete search history.

(56)           References Cited

U.S. PATENT DOCUMENTS

| | | | |
|---|---|---|---|
| 2013/0325759 A1* | 12/2013 | Rachevsky | G06V 10/764 |
| | | | 706/12 |
| 2017/0360325 A1 | 12/2017 | Hebert | |
| 2020/0129780 A1* | 4/2020 | Lachaine | A61N 5/1039 |
| 2020/0311557 A1* | 10/2020 | Jin | G06N 3/08 |
| 2021/0041519 A1* | 2/2021 | Piccini | G06T 11/008 |
| 2021/0319026 A1* | 10/2021 | Seth | G06N 5/04 |

OTHER PUBLICATIONS

"International Application Serial No. PCT/CA2021/050934, International Search Report mailed Apr. 5, 2022", 3 pgs.
"International Application Serial No. PCT/CA2021/050934, Written Opinion mailed Apr. 5, 2022", 5 pgs.

\* cited by examiner

FIG. 4A                  FIG. 4B

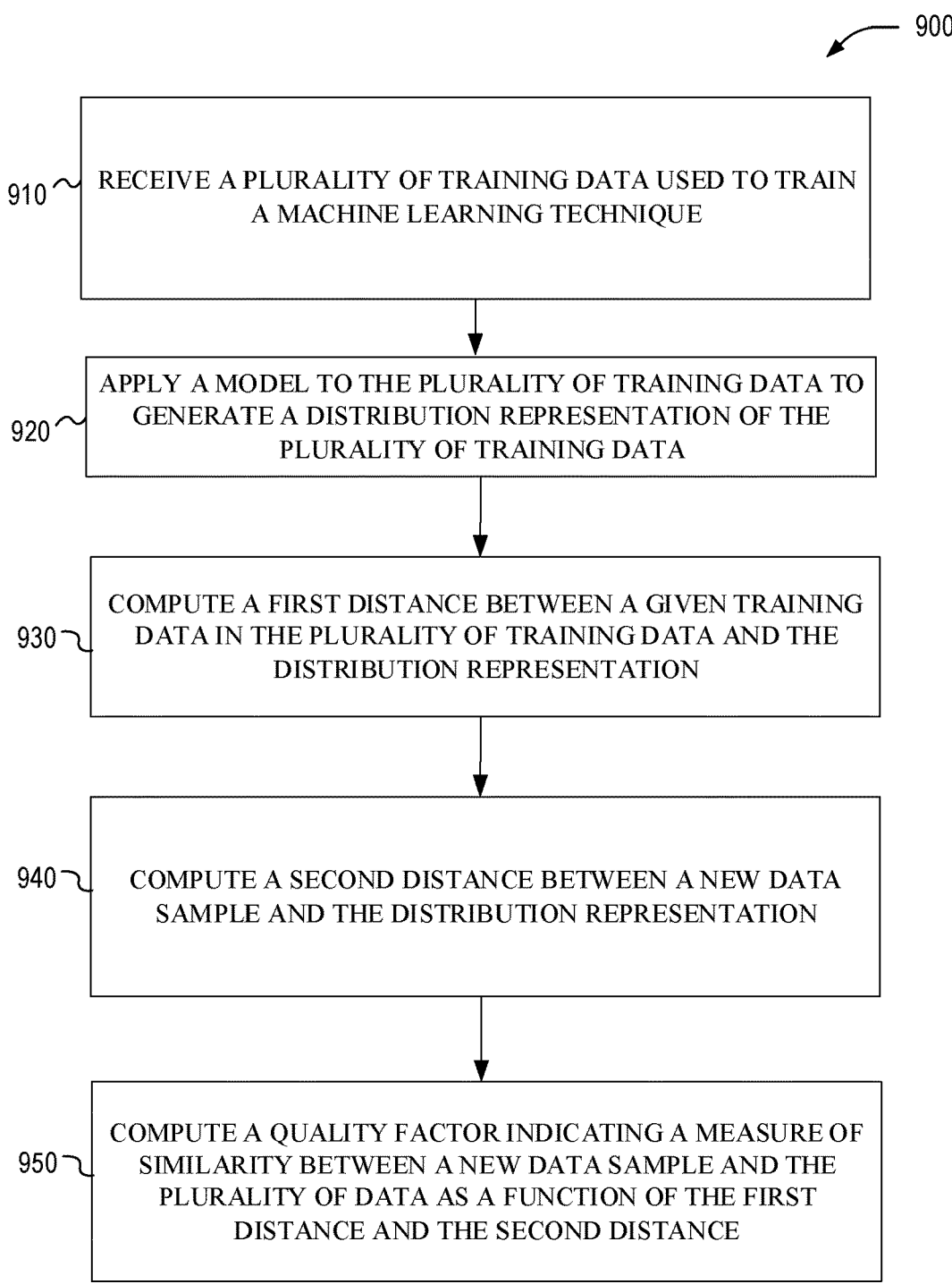

900

910 ~ RECEIVE A PLURALITY OF TRAINING DATA USED TO TRAIN A MACHINE LEARNING TECHNIQUE

920 ~ APPLY A MODEL TO THE PLURALITY OF TRAINING DATA TO GENERATE A DISTRIBUTION REPRESENTATION OF THE PLURALITY OF TRAINING DATA

930 ~ COMPUTE A FIRST DISTANCE BETWEEN A GIVEN TRAINING DATA IN THE PLURALITY OF TRAINING DATA AND THE DISTRIBUTION REPRESENTATION

940 ~ COMPUTE A SECOND DISTANCE BETWEEN A NEW DATA SAMPLE AND THE DISTRIBUTION REPRESENTATION

950 ~ COMPUTE A QUALITY FACTOR INDICATING A MEASURE OF SIMILARITY BETWEEN A NEW DATA SAMPLE AND THE PLURALITY OF DATA AS A FUNCTION OF THE FIRST DISTANCE AND THE SECOND DISTANCE

*FIG. 9*

IMAGE QUALITY RELATIVE TO MACHINE LEARNING DATA

PRIORITY APPLICATIONS

This application is a U.S. National Stage Filing under 35 U.S.C. § 371 from International Application No. PCT/CA2021/050824, filed on Jun. 17, 2021, and published as WO2022/261742 on Dec. 22, 2022; the benefit of priority of which is hereby claimed herein, and which application and publication is hereby incorporated herein by reference in its entirety.

TECHNICAL FIELD

Embodiments of the present disclosure pertain generally to measuring quality of an image relative to training data.

BACKGROUND

Radiation therapy (or "radiotherapy") can be used to treat cancers or other ailments in mammalian (e.g., human and animal) tissue. One such radiotherapy technique involves irradiation with a Gamma Knife, whereby a patient is irradiated by a large number of low-intensity gamma ray beams that converge with high intensity and high precision at a target (e.g., a tumor). In another embodiment, radiotherapy is provided using a linear accelerator, whereby a tumor is irradiated by high-energy particles (e.g., electrons, protons, ions, high-energy photons, and the like). The placement and dose of the radiation beam must be accurately controlled to ensure the tumor receives the prescribed radiation, and the placement of the beam should be such as to minimize damage to the surrounding healthy tissue, often called the organ(s) at risk (OARs). Radiation is termed "prescribed" because a physician orders a predefined amount of radiation to the tumor and surrounding organs similar to a prescription for medicine. Generally, ionizing radiation in the form of a collimated beam is directed from an external radiation source toward a patient.

A specified or selectable beam energy can be used, such as for delivering a diagnostic energy level range or a therapeutic energy level range. Modulation of a radiation beam can be provided by one or more attenuators or collimators (e.g., a multi-leaf collimator (MLC)). The intensity and shape of the radiation beam can be adjusted by collimation to avoid damaging healthy tissue (e.g., OARs) adjacent to the targeted tissue by conforming the projected beam to a profile of the targeted tissue.

The treatment planning procedure may include using a three-dimensional (3D) image of the patient to identify a target region (e.g., the tumor) and to identify critical organs near the tumor. Creation of a treatment plan can be a time-consuming process where a planner tries to comply with various treatment objectives or constraints (e.g., dose volume histogram (DVH), overlap volume histogram (OVH)), taking into account their individual importance (e.g., weighting) in order to produce a treatment plan that is clinically acceptable. This task can be a time-consuming trial-and-error process that is complicated by the various OARs because as the number of OARs increases (e.g., up to thirteen for a head-and-neck treatment), so does the complexity of the process. OARs distant from a tumor may be easily spared from radiation, while OARs close to or overlapping a target tumor may be difficult to spare.

Traditionally, for each patient, the initial treatment plan can be generated in an "offline" manner. The treatment plan can be developed well before radiation therapy is delivered, such as using one or more medical imaging techniques. Imaging information can include, for example, images from X-rays, computed tomography (CT), nuclear magnetic resonance (MR), positron emission tomography (PET), single-photon emission computed tomography (SPECT), or ultrasound. A health care provider, such as a physician, may use 3D imaging information indicative of the patient anatomy to identify one or more target tumors along with the OARs near the tumor(s). The health care provider can delineate the target tumor that is to receive a prescribed radiation dose using a manual technique, and the health care provider can similarly delineate nearby tissue, such as organs, at risk of damage from the radiation treatment. Alternatively, or additionally, an automated tool (e.g., ABAS provided by Elekta AB, Sweden) can be used to assist in identifying or delineating the target tumor and organs at risk. A radiation therapy treatment plan ("treatment plan") can then be created using an optimization technique based on clinical and dosimetric objectives and constraints (e.g., the maximum, minimum, and fraction of dose of radiation to a fraction of the tumor volume ("95% of target shall receive no less than 100% of prescribed dose"), and like measures for the critical organs). The optimized plan is comprised of numerical parameters that specify the direction, cross-sectional shape, and intensity of each radiation beam.

The treatment plan can then be later executed by positioning the patient in the treatment machine and delivering the prescribed radiation therapy directed by the optimized plan parameters. The radiation therapy treatment plan can include dose "fractioning," whereby a sequence of radiation treatments is provided over a predetermined period of time (e.g., 30-45 daily fractions), with each treatment including a specified fraction of a total prescribed dose. However, during treatment, the position of the patient and the position of the target tumor in relation to the treatment machine (e.g., linear accelerator—"linac") is very important in order to ensure the target tumor and not healthy tissue is irradiated.

Overview

In some aspects, systems and methods are provided for performing operations including: receiving a plurality of training data used to train a machine learning technique; applying a model to the plurality of training data to generate a distribution representation of the plurality of training data; determining that the plurality of training data correspond to periodic motion; in response to determining that the plurality of training data correspond to periodic motion, clustering the plurality of training data into a plurality of clusters each representative of an anatomic motion state; computing a first distance between a given training data in the plurality of training data and the distribution representation; computing a second distance between a new data sample and the distribution representation based on a given one of the plurality of clusters: computing a quality factor indicating a measure of similarity between a new data sample and the plurality of training data as a function of the first distance and the second distance: comparing the quality factor to a threshold value; and in response to determining that the quality factor exceeds the threshold value, increasing a confidence value associated with a result of applying the machine learning technique to the new data sample.

In some implementations, the quality factor is indicative of a confidence level of applying the machine learning technique to the new data sample.

3

In some implementations, the operations further comprise determining pixel intensity values for a plurality of training medical images.

In some implementations, applying the model comprises generating a Principal Component Analysis (PCA) representation of the plurality of training medical images based on the pixel intensity values.

In some implementations, the operations further comprise: applying a threshold to the PCA representation of the plurality of training medical images to retain a portion of a plurality of components of the PCA representation; and projecting the plurality of training medical images to the portion of the plurality of components of the PCA representation.

In some implementations, the operations further comprise: computing a training probability of a distribution of the plurality of components of the PCA representation for each of the plurality of training medical images; computing a new probability of a distribution associated with the new data sample relative to the plurality of components of the PCA representation; and comparing the new probability to the training probability of the distribution to generate the quality factor.

In some implementations, the operations further comprise: computing a plurality of distances by computing a Mahalanobis distance between each of the plurality of training medical images and the portion of the plurality of components of the PCA representation to generate a distribution of distances.

In some implementations, the operations further comprise: extracting a given percentile distance from the plurality of distances as the first distance; normalizing the second distance by the given percentile distance; and comparing the normalized second distance to a threshold to generate the quality factor.

In some implementations, the operations further comprise computing a plurality of distances for each of the plurality of clusters.

In some implementations, the operations further comprise: comparing the second distance to the plurality of distances: identifying a cluster of the plurality of clusters associated with a minimum distance that results from comparing the second distance to the plurality of distances: and computing the quality factor as a function of the first distance and the minimum distance.

In some implementations, the operations further comprise: determining pixel intensity values for a plurality of training medical images; and generating, for each of the plurality of clusters, a Principal Component Analysis (PCA) representation of the plurality of training medical images based on the pixel intensity values.

In some implementations, the operations further comprise: registering the plurality of training data based on a motion template to generate a motion registered training image set: applying the model to the motion registered training image set to generate a registered image distribution representation of the motion registered training image set: and registering the new data sample based on the motion template to generate a registered new data sample, wherein the second distance is computed based on a deviation between the registered new data sample and the registered image distribution representation.

In some implementations, the training data comprises a plurality of training medical images including at least one of a cine image, a magnetic resonance (MR) image, an ultrasound image, a kV image, or an x-ray image.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

FIG. 9 illustrates a method for computing a quality factor of a data sample relative to a training data set, according to some embodiments of the present disclosure.

DETAILED DESCRIPTION

Figure 1:
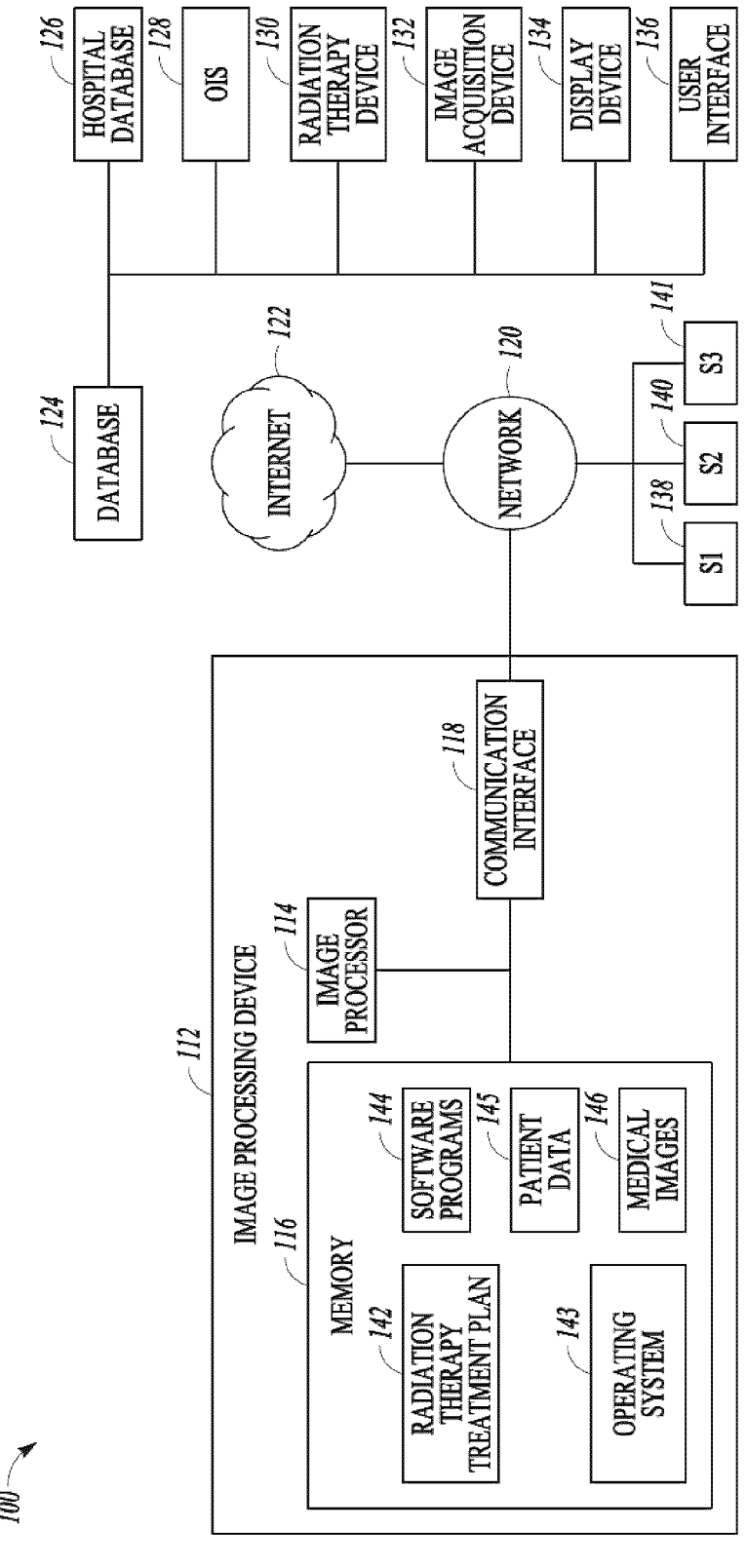
FIG. 1 illustrates an example radiotherapy system including a treatment modality selection device, according to some embodiments of the present disclosure.

In the following detailed description, reference is made to the accompanying drawings which form a part hereof, and which is shown by way of illustration-specific embodiments in which the present disclosure may be practiced. These embodiments, which are also referred to herein as "examples," are described in sufficient detail to enable those skilled in the art to practice the disclosure, and it is to be understood that the embodiments may be combined, or that other embodiments may be utilized and that structural, logical and electrical changes may be made without departing from the scope of the present disclosure. The following detailed description is, therefore, not be taken in a limiting sense, and the scope of the present disclosure is defined by the appended claims and their equivalents.

Typical machine learning systems train a machine learning model, such as a neural network, based on a set of training data. The training data is usually selected to represent a portion of a large population and may not account for every possible permutation of images representing the population. This is because training models based on every possible permutation would be very tedious and time consuming and would require a tremendous amount of resources. When applied to a new data point, such as a new medical image, the machine learning system can generate a prediction or estimation based on the previous behaviors observed from the training data used to train the machine learning system. However, the reliability and accuracy of the output or prediction or estimation generated by the machine learning system depends on how similar the new data point, such as the new medical image, is to the training data used to train the machine learning system. Without a means for assessing the similarity between a new data point and the training data set, the outputs generated by the machine learning systems can become random and lose value.

The disclosed embodiments provide a technique that verifies whether a new data sample, such as a new medical image, is represented by a training set used to train a machine learning (ML) model. The disclosed embodiments provide a quality factor that indicates whether a new image is suitable to be processed by the ML model. Based on the value of the quality factor, a determination can be made as to the quality of the output of the ML model when applied to the new data sample (e.g., medical image). Specifically the quality factor can be indicative of whether the new data sample is in the domain of interpolation, rather than extrapolation, of application of the ML model. Specifically, if the new data sample is similar to the training data (e.g., medical images) used to train the ML model, then the quality factor indicates that the outcome or prediction or estimation of the ML model applied to the new data sample is likely good: otherwise, if the new data sample is dissimilar to the training data, the quality factor indicates that the output of the ML model as applied to the new data sample is more random. In this way, an objective of the disclosed techniques is to measure how far a new data sample is from the training data set distribution and whether the new data sample is within a representation of the training set or an outlier.

The disclosed embodiments generate such a quality factor by receiving a plurality of training data (e.g., medical images) used to train a machine learning technique. The disclosed embodiments apply a model to the plurality of training data to generate a distribution representation of the plurality of training data and compute a first distance between a given training data in the plurality of training data and the distribution representation. The disclosed embodiments compute a second distance between a new data sample and the distribution representation and compute a quality factor indicating a measure of similarity between a new data sample and the plurality of data as a function of the first distance and the second distance. In some cases, the quality factor is compared to a threshold value, and in response to determining that the quality factor exceeds the threshold value, a confidence value associated with a result of applying the machine learning technique to the new data sample is increased.

In this way, the quality factor generated by the disclosed techniques can inform a system as to the accuracy of prediction or estimation provided by applying a ML model to a new data sample (e.g., medical image). This saves computational resources and the time and expense usually incurred by typical systems by avoiding application of an ML model to a new data sample entirely if the quality factor is low. In some cases, weights associated with outputs of the ML model can be modified on the basis of the quality factor, such as to avoid erroneous results that rely too heavily on the outputs of the ML model if the quality factor is relatively low.

FIG. 1 illustrates an example radiotherapy system 100 for providing radiation therapy to a patient, according to some embodiments. The radiotherapy system 100 includes an image processing device 112. The image processing device 112 may be connected to a network 120. The network 120 may be connected to the Internet 122. The network 120 can connect the image processing device 112 with one or more of a database 124, a hospital database 126, an oncology information system (OIS) 128, a radiation therapy device 130, an image acquisition device 132, a display device 134, and a user interface 136. The image processing device 112 can be configured to generate radiation therapy treatment plans 142 to be used by the radiation therapy device 130.

The image processing device 112 may include a memory device 116, a processor 114, and a communication interface 118. The memory device 116 may store computer-executable instructions, such as an operating system 143, radiation therapy treatment plans 142 (e.g., original treatment plans, adapted treatment plans and the like), software programs 144 (e.g., artificial intelligence, deep learning, neural networks, radiotherapy treatment plan software), and any other computer-executable instructions to be executed by the processor 114.

In one embodiment, the software programs 144 may convert medical images of one format (e.g., MRI) to another format (e.g., CT) by producing synthetic images, such as pseudo-CT images. For instance, the software programs 144 may include image processing programs to train a predictive model for converting a medical image 146 in one modality (e.g., an MRI image) into a synthetic image of a different modality (e.g., a pseudo CT image): alternatively, the trained predictive model may convert a CT image into an MRI image. In another embodiment, the software programs 144 may register the patient image (e.g., a CT image or an MR image) with that patient's dose distribution (also represented as an image) so that corresponding image voxels and dose voxels are associated appropriately by the network. In yet another embodiment, the software programs 144 may substitute functions of the patient images or processed versions of the images that emphasize some aspect of the image information. Such functions might emphasize edges or differences in voxel textures, or any other structural aspect useful to neural network learning. In another embodiment, the software programs 144 may substitute functions of the dose distribution that emphasize some aspect of the dose information. Such functions might emphasize steep gradients around the target or any other structural aspect useful to neural network learning. The memory device 116 may store data, including medical images 146, patient data 145, and other data required to create and implement a radiation therapy treatment plan 142.

In addition to the memory device 116 storing the software programs 144, it is contemplated that software programs 144 may be stored on a removable computer medium, such as a hard drive, a computer disk, a CD-ROM, a DVD, a HD, a Blu-Ray DVD, USB flash drive, a SD card, a memory stick, or any other suitable medium: and the software programs 144 when downloaded to image processing device 112 may be executed by image processor 114.

The processor 114 may be communicatively coupled to the memory device 116, and the processor 114 may be configured to execute computer-executable instructions stored thereon. The processor 114 may send or receive medical images 146 to memory device 116. For example, the processor 114 may receive medical images 146 from the image acquisition device 132 via the communication interface 118 and network 120 to be stored in memory device 116. The processor 114 may also send medical images 146 stored in memory device 116 via the communication interface 118 to the network 120 to be either stored in database 124 or the hospital database 126.

Further, the processor 114 may utilize software programs 144 (e.g., a treatment planning software) along with the medical images 146 and patient data 145 to create the radiation therapy treatment plan 142. Medical images 146 may include information such as imaging data associated with a patient anatomical region, organ, or volume of interest segmentation data. The medical images 146 may include or be associated with metadata that specifies the periodic motion phase of a target region depicted in the medical images 146 (e.g., the respiratory phase of a breathing cycle depicted in the medical images 146). Patient data 145 may include information such as (1) functional organ modeling data (e.g., serial versus parallel organs, appropriate dose response models, etc.); (2) radiation dosage data (e.g., DVH information); or (3) other clinical information about the patient and course of treatment (e.g., other surgeries, chemotherapy, previous radiotherapy, etc.). The medical images 146 may be received from or be associated with a device that measures or determines a motion phase of periodic motion of a target region depicted in the images.

In addition, the processor 114 may utilize software programs to generate intermediate data such as updated parameters to be used, for example, by a machine learning model, such as a neural network model: or generate intermediate 2D or 3D images, which may then subsequently be stored in memory device 116. The processor 114 may subsequently transmit the executable radiation therapy treatment plan 142 via the communication interface 118 to the network 120 to the radiation therapy device 130, where the radiation therapy plan will be used to treat a patient with radiation. In addition, the processor 114 may execute software programs 144 to implement functions such as image conversion, image segmentation, deep learning, neural networks, and artificial intelligence. For instance, the processor 114 may execute software programs 144 that train or contour a medical image: such software programs 144 when executed, may train a boundary detector or utilize a shape dictionary.

The processor 114 may be a processing device, include one or more general-purpose processing devices such as a microprocessor, a central processing unit (CPU), a graphics processing unit (GPU), an accelerated processing unit (APU), or the like. More particularly, the processor 114 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processor 114 may also be implemented by one or more special-purpose processing devices such as an application-specific integrated circuit (ASIC), a field programmable gate array (FPGA), a digital signal processor (DSP), a System on a Chip (SoC), or the like. As would be appreciated by those skilled in the art, in some embodiments, the processor 114 may be a special-purpose processor, rather than a general-purpose processor. The processor 114 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processor 114 may also include graphical processing units such as a GPU from the GeForce®, Quadro®, Tesla® family manufactured by Nvidia™, GMA, Iris™ family manufactured by Intel™, or the Radeon™ family manufactured by AMD™. The processor 114 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor (for example, a multi-core design or a plurality of processors each having a multi-core design). The processor 114 can execute sequences of computer program instructions, stored in memory device 116, to perform various operations, processes, methods that will be explained in greater detail below.

The memory device 116 can store medical images 146. In some embodiments, the medical images 146 may include one or more MRI images (e.g., 2D MRI, 3D MRI, 2D streaming MRI, four-dimensional (4D) MRI, 4D volumetric MRI, 4D cine MRI, etc.), functional MRI images (e.g., fMRI, DCE-MRI, diffusion MRI), CT images (e.g., 2D CT, cone beam CT, 3D CT, 4D CT), ultrasound images (e.g., 2D ultrasound, 3D ultrasound, 4D ultrasound), one or more projection images representing views of an anatomy depicted in the MRI, synthetic CT (pseudo-CT), and/or CT images at different angles of a gantry relative to a patient axis, PET images, X-ray images, fluoroscopic images, radiotherapy portal images, SPECT images, computer-generated synthetic images (e.g., pseudo-CT images), aperture images, graphical aperture image representations of MLC leaf positions at different gantry angles, and the like. Further, the medical images 146 may also include medical image data, for instance, training images, ground truth images, contoured images, and dose images. In an embodiment, the medical images 146 may be received from the image acquisition device 132. Accordingly, image acquisition device 132 may include an MRI imaging device, a CT imaging device, a PET imaging device, an ultrasound imaging device, a fluoroscopic device, a SPECT imaging device, an integrated linac and MRI imaging device, or other medical imaging devices for obtaining the medical images of the patient. The medical images 146 may be received and stored in any type of data or any type of format that the image processing device 112 may use to perform operations consistent with the disclosed embodiments.

The memory device 116 may be a non-transitory computer-readable medium, such as a read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a CD-ROM, a DVD or other optical storage, a cassette tape, other magnetic storage device, or any other non-transitory medium that may be used to store information including image, data, or computer executable instructions (e.g., stored in any format) capable of being accessed by the processor 114, or any other type of computer device. The computer program instructions can be accessed by the processor 114, read from the ROM, or any other suitable memory location, and loaded into the RAM for execution by the processor 114. For example, the memory device 116 may store one or more software applications. Software applications stored in the memory device 116 may include, for example, an operating system 143 for common computer systems as well as for software-controlled devices. Further, the memory device 116 may store an entire software application, or only a part of a software application, that is executable by the processor 114. For example, the memory device 116 may store one or more radiation therapy treatment plans 142.

The image processing device 112 can communicate with the network 120 via the communication interface 118, which can be communicatively coupled to the processor 114 and the memory device 116. The communication interface 118 may provide communication connections between the image processing device 112 and radiotherapy system 100 components (e.g., permitting the exchange of data with external devices). For instance, the communication interface 118 may, in some embodiments, have appropriate interfacing circuitry to connect to the user interface 136, which may be a hardware keyboard, a keypad, or a touch screen through which a user may input information into radiotherapy system 100.

Communication interface 118 may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a WiFi adaptor), a telecommunication adaptor (e.g., 3G, 4G/LTE and the like), and the like. Communication interface 118 may include one or more digital and/or analog communication devices that permit image processing device 112 to communicate with other machines and devices, such as remotely located components, via the network 120.

The network 120 may provide the functionality of a local area network (LAN), a wireless network, a cloud computing environment (e.g., software as a service, platform as a service, infrastructure as a service, etc.), a client-server, a wide area network (WAN), and the like. For example, network 120 may be a LAN or a WAN that may include other systems S1 (138), S2 (140), and S3 (141). Systems S1, S2, and S3 may be identical to image processing device 112 or may be different systems. In some embodiments, one or more systems in network 120 may form a distributed computing/simulation environment that collaboratively performs the embodiments described herein. In some embodiments, one or more systems S1, S2, and S3 may include a CT scanner that obtains CT images (e.g., medical images 146). In addition, network 120 may be connected to Internet 122 to communicate with servers and clients that reside remotely on the internet.

Therefore, network 120 can allow data transmission between the image processing device 112 and a number of various other systems and devices, such as the OIS 128, the radiation therapy device 130, and the image acquisition device 132. Further, data generated by the OIS 128 and/or the image acquisition device 132 may be stored in the memory device 116, the database 124, and/or the hospital database 126. The data may be transmitted/received via network 120, through communication interface 118 in order to be accessed by the processor 114, as required.

The image processing device 112 may communicate with database 124 through network 120 to send/receive a plurality of various types of data stored on database 124. For example, database 124 may include machine data (control points) that includes information associated with a radiation therapy device 130, image acquisition device 132, or other machines relevant to radiotherapy. Machine data information may include control points, such as radiation beam size, arc placement, beam on and off time duration, machine parameters, segments, MLC configuration, gantry speed, MRI pulse sequence, and the like. Database 124 may be a storage device and may be equipped with appropriate database administration software programs. One skilled in the art would appreciate that database 124 may include a plurality of devices located either in a central or a distributed manner.

In some embodiments, database 124 may include a processor-readable storage medium (not shown). While the processor-readable storage medium in an embodiment may be a single medium, the term "processor-readable storage medium" should be taken to include a single medium or multiple media (e.g., a centralized or distributed database, and/or associated caches and servers) that store the one or more sets of computer-executable instructions or data. The term "processor-readable storage medium" shall also be taken to include any medium that is capable of storing or encoding a set of instructions for execution by a processor and that cause the processor to perform any one or more of the methodologies of the present disclosure. The term "processor-readable storage medium" shall accordingly be taken to include, but not be limited to, solid-state memories and optical and magnetic media. For example, the processor-readable storage medium can be one or more volatile, non-transitory, or non-volatile tangible computer-readable media.

Image processor 114 may communicate with database 124 to read images into memory device 116 or store images from memory device 116 to database 124. For example, the database 124 may be configured to store a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DIMCOM) data, projection images, graphical aperture images, etc.) that the database 124 received from image acquisition device 132. Database 124 may store data to be used by the image processor 114 when executing software program 144 or when creating radiation therapy treatment plans 142. Database 124 may store the data produced by the trained machine learning mode, such as a neural network including the network parameters constituting the model learned by the network and the resulting estimated data. As referred to herein, "estimate" or "estimated" can be used interchangeably with "predict" or "predicted" and should be understood to have the same meaning. The image processing device 112 may receive the imaging data, such as a medical image 146 (e.g., 2D MRI slice images, CT images, 2D Fluoroscopy images, X-ray images, 3DMRI images, 4D MRI images, projection images, graphical aperture images, image contours, etc.) from the database 124, the radiation therapy device 130 (e.g., an MR-linac), and/or the image acquisition device 132 to generate a treatment plan 142.

In an embodiment, the radiotherapy system 100 can include an image acquisition device 132 that can acquire medical images (e.g., MRI images, 3D MRI, 2D streaming MRI, 4D volumetric MRI, CT images, cone-Beam CT, PET images, functional MRI images (e.g., fMRI, DCE-MRI and diffusion MRI), X-ray images, fluoroscopic image, ultrasound images, radiotherapy portal images, SPECT images, and the like) of the patient. Image acquisition device 132 may, for example, be an MRI imaging device, a CT imaging device, a PET imaging device, an ultrasound device, a fluoroscopic device, a SPECT imaging device, or any other suitable medical imaging device for obtaining one or more medical images of the patient. Images acquired by the image acquisition device 132 can be stored within database 124 as either imaging data and/or test data. By way of example, the images acquired by the image acquisition device 132 can also be stored by the image processing device 112, as medical image 146 in memory device 116.

In an embodiment, for example, the image acquisition device 132 may be integrated with the radiation therapy device 130 as a single apparatus (e.g., an MR-linac). Such an MR-linac can be used, for example, to determine a location of a target organ or a target tumor in the patient, so as to direct radiation therapy accurately according to the radiation therapy treatment plan 142 to a predetermined target.

The image acquisition device 132 can be configured to acquire one or more images of the patient's anatomy for a region of interest (e.g., a target organ, a target tumor, or both). Each image, typically a 2D image or slice, can include one or more parameters (e.g., a 2D slice thickness, an orientation, and a location, etc.). In an embodiment, the image acquisition device 132 can acquire a 2D slice in any orientation. For example, an orientation of the 2D slice can include a sagittal orientation, a coronal orientation, or an axial orientation. The processor 114 can adjust one or more parameters, such as the thickness and/or orientation of the 2D slice, to include the target organ and/or target tumor. In an embodiment, 2D slices can be determined from information such as a 3D MRI volume. Such 2D slices can be acquired by the image acquisition device 132 in "real-time" while a patient is undergoing radiation therapy treatment, for example, when using the radiation therapy device 130, with "real-time" meaning acquiring the data in at least milliseconds or less.

The image processing device 112 may generate and store radiation therapy treatment plans 142 for one or more patients. The radiation therapy treatment plans 142 may provide information about a particular radiation dose to be applied to each patient. The radiation therapy treatment plans 142 may also include other radiotherapy information, such as control points including beam angles, gantry angles, beam intensity, dose-histogram-volume information, the number of radiation beams to be used during therapy, the dose per beam, and the like.

The image processor 114 may generate the radiation therapy treatment plan 142 by using software programs 144 such as treatment planning software (such as Monaco®, manufactured by Elekta AB of Stockholm, Sweden). In order to generate the radiation therapy treatment plans 142, the image processor 114 may communicate with the image acquisition device 132 (e.g., a CT device, an MRI device, a PET device, an X-ray device, an ultrasound device, etc.) to access images of the patient and to delineate a target, such as a tumor, to generate contours of the images. In some embodiments, the delineation of one or more OARs, such as healthy tissue surrounding the tumor or in close proximity to the tumor, may be required. Therefore, segmentation of the OAR may be performed when the OAR is close to the target tumor. In addition, if the target tumor is close to the OAR (e.g., prostate in near proximity to the bladder and rectum), then by segmenting the OAR from the tumor, the radiotherapy system 100 may study the dose distribution not only in the target but also in the OAR.

In order to delineate a target organ or a target tumor from the OAR, medical images, such as MRI images, CT images, PET images, fMRI images, X-ray images, ultrasound images, radiotherapy portal images, SPECT images, and the like, of the patient undergoing radiotherapy may be obtained non-invasively by the image acquisition device 132 to reveal the internal structure of a body part. Based on the information from the medical images, a 3D structure of the relevant anatomical portion may be obtained and used to generate a contour of the image. Contours of the image can include data overlaid on top of the image that delineates one or more structures of the anatomy. In some cases, the contours can be files associated with respective images that specify the coordinates or 2D or 3D locations of various structures of the anatomy depicted in the images.

In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Other parameters that may be considered include the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker using a program such as MONACO™ manufactured by Elekta AB of Stockholm, Sweden) or automatically (e.g., using a program such as the Atlas-based auto-segmentation software, ABAS™, manufactured by Elekta AB of Stockholm, Sweden). In certain embodiments, the 3D structure of a target tumor or an OAR may be generated automatically by the treatment planning software.

After the target tumor and the OAR(s) have been located and delineated, a dosimetrist, physician, or healthcare worker may determine a dose of radiation to be applied to the target tumor, as well as any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and beam-on times. During the inverse-planning process, the physician may define dose constraint parameters that set bounds on how much radiation an OAR may receive (e.g., defining full dose to the tumor target and zero dose to any OAR: defining 95% of dose to the target tumor: defining that the spinal cord, brain stem, and optic structures receive ≤45 Gy, ≤55 Gy and <54 Gy, respectively). The result of inverse planning may constitute a radiation therapy treatment plan 142 that may be stored in memory device 116 or database 124. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, the image processing device 112 can generate a tailored radiation therapy treatment plan 142 having these parameters in order for the radiation therapy device 130 to provide radiotherapy treatment to the patient.

In addition, the radiotherapy system 100 may include a display device 134 and a user interface 136. The display device 134 may include one or more display screens that display medical images, interface information, treatment planning parameters (e.g., projection images, graphical aperture images, contours, dosages, beam angles, etc.) treatment plans, a target, localizing a target and/or tracking a target, or any related information to the user. The user interface 136 may be a keyboard, a keypad, a touch screen or any type of device that a user may use to input information to radiotherapy system 100. Alternatively, the display device 134 and the user interface 136 may be integrated into a device such as a tablet computer (e.g., Apple iPad®, Lenovo ThinkPad®, Samsung Galaxy®, etc.).

Furthermore, any and all components of the radiotherapy system 100 may be implemented as a virtual machine (e.g., VMWare, Hyper-V, and the like). For instance, a virtual machine can be software that functions as hardware. Therefore, a virtual machine can include at least one or more virtual processors, one or more virtual memories, and one or more virtual communication interfaces that together function as hardware. For example, the image processing device 112, the OIS 128, and the image acquisition device 132 could be implemented as a virtual machine. Given the processing power, memory, and computational capability available, the entire radiotherapy system 100 could be implemented as a virtual machine.

In some examples, the image processing device 112 can generate a quality factor or compute a quality factor that indicates how well a new data sample correlates with training data used previously to train a machine learning model. In some cases, the quality factor determination can be part of the flow diagram for deep learning discussed in connection with FIG. 7 below. In order to generate the quality factor, the image processing device 112 can access a training data set used to train the machine learning model, such as the training data included among the inputs 704 to the deep learning model. The image processing device 112 applies a model to the training data to generate a distribution representation of the training data. The image processing device 112 computes distances between each data sample in the training data and the distribution representation. The image processing device 112 can receive a new data sample and compute a distance between the new data sample and the distribution representation. The image processing device 112 can then generate the quality factor indicating a measure of similarity between the new data sample and the plurality of data as a function of a distance of a given data sample in the training data and the distribution representation and the distance between the new data sample and the distribution representation.

In one example, the image processing device 112 can generate the distribution representation of the plurality of training data based on a Principal Component Analysis (PCA) model. Specifically, the image processing device 112 can determine pixel intensity values of the training data (which can include training medical images) and generate a Principal Component Analysis (PCA) representation of the plurality of training data based on the pixel intensity values. The image processing device 112 applies a threshold to the PCA representation of the plurality of training data to retain a portion of a plurality of components of the PCA representation to provide a reduced PCA representation, which can reduce noise in the training data. This reduced PCA representation can be used as the distribution representation of the plurality of training data.

In one example, after generating the reduced PCA representation, the image processing device 112 computes distances between each data sample in the training data and the distribution representation. This can be performed by projecting the plurality of training data to the portion of the plurality of components of the PCA representation. Each data sample in the data (e.g., each medical image) is then projected on the reduced PCA base. The image processing device 112 can then compute a Mahalanobis distance for all of the reduced PCA values in the training set to provide the distances between each data sample in the training data and the distribution representation. Namely, the image processing device 112 computes a plurality of distances between each data sample in the training data and the distribution representation by computing a Mahalanobis distance between each of the plurality of training data and the portion of the plurality of components of the PCA representation.

The image processing device 112 generates a distribution of distances based on the computed Mahalanobis distance between each of the plurality of training data and the portion of the plurality of components of the PCA representation. The image processing device 112 normalizes the distribution of distances by the $95^{th}$ percentile distance (or some other given quantile or percentile distance). In some examples, the image processing device 112 computes the Mahalanobis distance between a new data sample and the distribution representation. The image processing device 112 can normalize the Mahalanobis distance by the $95^{th}$ percentile distance or the other given quantile or percentile distance. The image processing device 112 can then compare the normalized distance of the new data sample to the configurable threshold or the normalized distribution of distances. If the normalized distance is above the configurable threshold, the image processing device 112 can determine that the new data sample is an outlier and can indicate that further measurement or application of the ML model to the new data sample would result in poor prediction. In response, the image processing device 112 can indicate a low level of confidence for the new data sample. If the normalized distance is within or below the configurable threshold, the image processing device 112 can determine that the new data sample is similar to the training data and can indicate that further measurement or application of the ML model to the new data sample would result in a good prediction. In response, the image processing device 112 can indicate a higher level of confidence for the new data sample.

In some examples, the image processing device 112 computes a training probability of a distribution of the plurality of components of the PCA representation for each of the plurality of training data (e.g., medical images). When a new data sample (e.g., a new medical image) is received, the image processing device 112 computes a new probability of a distribution associated with the new data sample relative to the plurality of components of the PCA representation. The image processing device 112 generates the quality factor based on a comparison between the new probability and the training probability.

In some examples, the image processing device 112 analyzes the training data (e.g., the training medical images) to determine that the training data corresponds to periodic (physiological) motion. In response, the image processing device 112 clusters the plurality of training data into a plurality of clusters which represent a different anatomic motion (physiological) state. For example, the physiological motion can correspond to breathing. In this case, three clusters can be used, a first of which corresponds to start of inhalation, a second of which corresponds to mid-ventilation, and a third of which corresponds to start of exhalation. In another example, the physiological motion can correspond to heartbeat phases. This clustering can be performed prior to the generation of the reduced PCA representation. After clustering the training data, the image processing device 112 can generate a reduced PCA representation, such as by determining pixel intensity values of the training data (which can include training medical images) and generating the PCA representation of the clustered plurality of training data based on the pixel intensity values. The image processing device 112 applies a threshold to the PCA representation of the plurality of training data to retain a portion of a plurality of components of the PCA representation to provide a reduced PCA representation.

The image processing device 112 can compute a plurality of distances for each of the plurality of clusters. Namely, the image processing device 112 can generate a first set of distances or a normalized distance for a first collection of data samples that are associated with a first cluster based on the reduced PCA representation. Specifically, the image processing device 112 can compute a distribution of distances for the data samples associated with the first cluster by computing a Mahalanobis distance between each of the plurality of training data in the first cluster and the reduced PCA representation of the entire data set or a PCA representation of just the data samples that are associated with the first cluster. The image processing device 112 normalizes the distribution of distances by the $95^{th}$ percentile distance (or some other given quantile or percentile distance) for the first cluster and associates this distribution of distances with the first cluster. Similarly, the image processing device 112 can generate a second set of distances or a normalized distance for a second collection of data samples that are associated with a second cluster based on the reduced PCA representation. Specifically, the image processing device 112 can compute a distribution of distances for the data samples associated with the second cluster by computing a Mahalanobis distance between each of the plurality of training data in the second cluster and the reduced PCA representation of the entire data set or a PCA representation of just the data samples that are associated with the second cluster. The image processing device 112 normalizes the distribution of distances by the $95^{th}$ percentile distance (or some other given quantile or percentile distance) for the second cluster and associates this distribution of distances with the second cluster. This results or generates an ordered set of PCAs for each cluster of the plurality of clusters.

The image processing device 112 can receive a new data sample (e.g., a new medical image) and can compute a Mahalanobis distance between a new data sample and the distribution representation, such as the ordered set of PCAs. The image processing device 112 can normalize the Mahalanobis distance by the $95^{th}$ percentile distance or the other given quantile or percentile distance. The image processing device 112 can compare the normalized distance of the new data sample to the normalized distances of each cluster. The image processing device 112 can identify a cluster of the plurality of clusters that is associated with a minimum distance between the normalized distance of the new data sample to the normalized distances of each cluster. For example, the image processing device 112 can compute a first difference between the normalized distance of the new data sample and the normalized distance of a first cluster.

Next, the image processing device 112 can compute a second difference between the normalized distance of the new data sample and the normalized distance of a second cluster. The image processing device 112 compares the first difference to the second difference. In response to determining that the second distance is smaller than the first distance, the image processing device 112 can determine that the second distance is the minimum distance. As a result, the image processing device 112 can select the second cluster associated with the second distance for generating the quality factor. Namely, the image processing device 112 can compare the second difference to a specified threshold to generate the quality factor. For example, if the second difference is lower than the threshold, the image processing device 112 can determine that the new data sample is similar to the second cluster of training data and that application of the ML model to the new data sample may result in a good prediction or estimation. If the second difference is greater than the threshold, the image processing device 112 can determine that the new data sample is dissimilar to the second cluster of training data and that application of the ML model to the new data sample may result in a poor prediction or estimation. Based on this, the image processing device 112 can associate a confidence level with application of the ML model to the new data sample.

In some examples, the image processing device 112 registers the training data (e.g., the training medical images) based on a motion template to generate a motion-registered training image set. This registration can be performed prior to the generation of the reduced PCA representation. After registering the training data, the image processing device 112 can generate a reduced PCA representation, such as by determining pixel intensity values of the training data (which can include training medical images) and generating the PCA representation of the registered plurality of training data based on the pixel intensity values. The image processing device 112 applies a threshold to the PCA representation of the plurality of training data to retain a portion of a plurality of components of the PCA representation to provide a reduced PCA representation. In this way, the image processing device 112 applies a model to the motion-registered training image set to generate a registered image distribution representation of the motion registered training image set.

The image processing device 112 generates a distribution of distances based on the computed Mahalanobis distance between each of the plurality of motion-registered training data and the portion of the plurality of components of the PCA representation. The image processing device 112 normalizes the distribution of distances by the $95^{th}$ percentile distance (or some other given quantile or percentile distance). The image processing device 112 can receive a new data sample (e.g., a new medical image). The image processing device 112 registers the new data sample based on the motion template to generate a motion-registered new data sample. The image processing device 112 then computes the distance between the motion-registered new data sample and the registered image distribution representation of the motion-registered training image set. For example, the image processing device 112 can compute a Mahalanobis distance between the motion registered new data sample and the motion registered distribution representation. The image processing device 112 can normalize the Mahalanobis distance of the new data sample by the $95^{th}$ percentile distance or the other given quantile or percentile distance. The image processing device 112 can then compare the normalized distance of the new data sample to the configurable threshold or the normalized distribution of distances. If the normalized distance is above the configurable threshold, the image processing device 112 can determine that the new data sample is an outlier and can indicate that further measurement or application of the ML model to the new data sample would result in poor prediction. In response, the image processing device 112 can indicate a low level of confidence for the new data sample. If the normalized distance is within or below the configurable threshold, the image processing device 112 can determine that the new data sample is similar to the training data and can indicate that further measurement or application of the ML model to the new data sample would result in a good prediction. In response, the image processing device 112 can indicate a higher level of confidence for the new data sample.

Figure 2A:
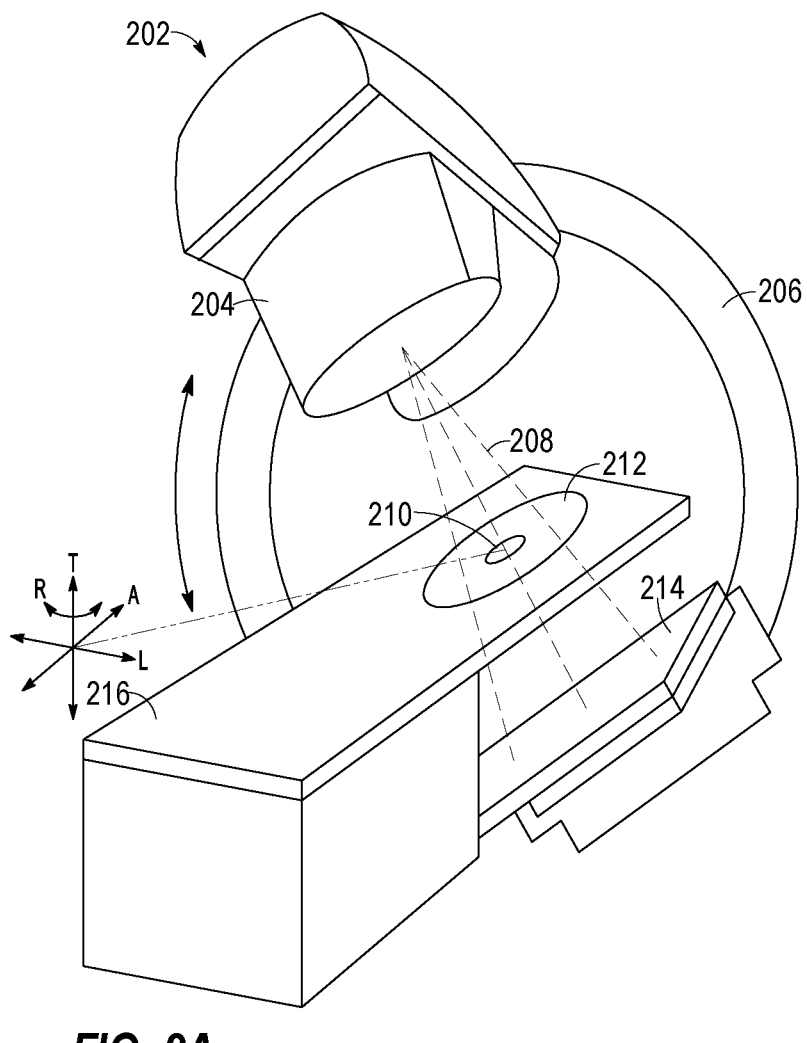
FIG. 2A illustrates an example radiation therapy system that can include radiation therapy output configured to provide a therapy beam, according to some embodiments of the present disclosure.

FIG. 2A illustrates an example radiation therapy device 202 that may include a radiation source, such as an X-ray source or a linear accelerator, a couch 216, an imaging detector 214, and a radiation therapy output 204. The radiation therapy device 202 may be configured to emit a radiation beam 208 to provide therapy to a patient. The radiation therapy output 204 can include one or more attenuators or collimators, such as an MLC as described in the illustrative embodiment of FIG. 5, below.

Referring back to FIG. 2A, a patient can be positioned in a region 212 and supported by the treatment couch 216 to receive a radiation therapy dose, according to a radiation therapy treatment plan. The radiation therapy output 204 can be mounted or attached to a gantry 206 or other mechanical support. One or more chassis motors (not shown) may rotate the gantry 206 and the radiation therapy output 204 around couch 216 when the couch 216 is inserted into the treatment area. In an embodiment, gantry 206 may be continuously rotatable around couch 216 when the couch 216 is inserted into the treatment area. In another embodiment, gantry 206 may rotate to a predetermined position when the couch 216 is inserted into the treatment area. For example, the gantry 206 can be configured to rotate the therapy output 204 around an axis ("A"). Both the couch 216 and the radiation therapy output 204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch's 216 movements or rotations in order to properly position the patient in or out of the radiation beam 208 according to a radiation therapy treatment plan. Both the couch 216 and the gantry 206 are independently moveable from one another in multiple degrees of freedom, which allows the patient to be positioned such that the radiation beam 208 can precisely target the tumor. The MLC may be integrated and included within gantry 206 to deliver the radiation beam 208 of a certain shape.

The coordinate system (including axes A, T, and L) shown in FIG. 2A can have an origin located at an isocenter 210. The isocenter 210 can be defined as a location where the central axis of the radiation beam 208 intersects the origin of a coordinate axis, such as to deliver a prescribed radiation dose to a location on or within a patient. Alternatively, the isocenter 210 can be defined as a location where the central axis of the radiation beam 208 intersects the patient for various rotational positions of the radiation therapy output 204 as positioned by the gantry 206 around the axis A. As discussed herein, the gantry angle corresponds to the position of gantry 206 relative to axis A, although any other axis or combination of axes can be referenced and used to determine the gantry angle.

Gantry 206 may also have an attached imaging detector 214. The imaging detector 214 is preferably located opposite to the radiation source, and in an embodiment, the imaging detector 214 can be located within a field of the therapy beam 208.

The imaging detector 214 can be mounted on the gantry 206 (preferably opposite the radiation therapy output 204), such as to maintain alignment with the therapy beam 208. The imaging detector 214 rotates about the rotational axis as the gantry 206 rotates. In an embodiment, the imaging detector 214 can be a flat panel detector (e.g., a direct detector or a scintillator detector). In this manner, the imaging detector 214 can be used to monitor the therapy beam 208 or the imaging detector 214 can be used for imaging the patient's anatomy, such as portal imaging. The control circuitry of radiation therapy device 202 may be integrated within system 100 or remote from it.

In an illustrative embodiment, one or more of the couch 216, the therapy output 204, or the gantry 206 can be automatically positioned, and the therapy output 204 can establish the therapy beam 208 according to a specified dose for a particular therapy delivery instance. A sequence of therapy deliveries can be specified according to a radiation therapy treatment plan, such as using one or more different orientations or locations of the gantry 206, couch 216, or therapy output 204. The therapy deliveries can occur sequentially, but can intersect in a desired therapy locus on or within the patient, such as at the isocenter 210. A prescribed cumulative dose of radiation therapy can thereby be delivered to the therapy locus while damage to tissue near the therapy locus can be reduced or avoided.

Figure 2B:
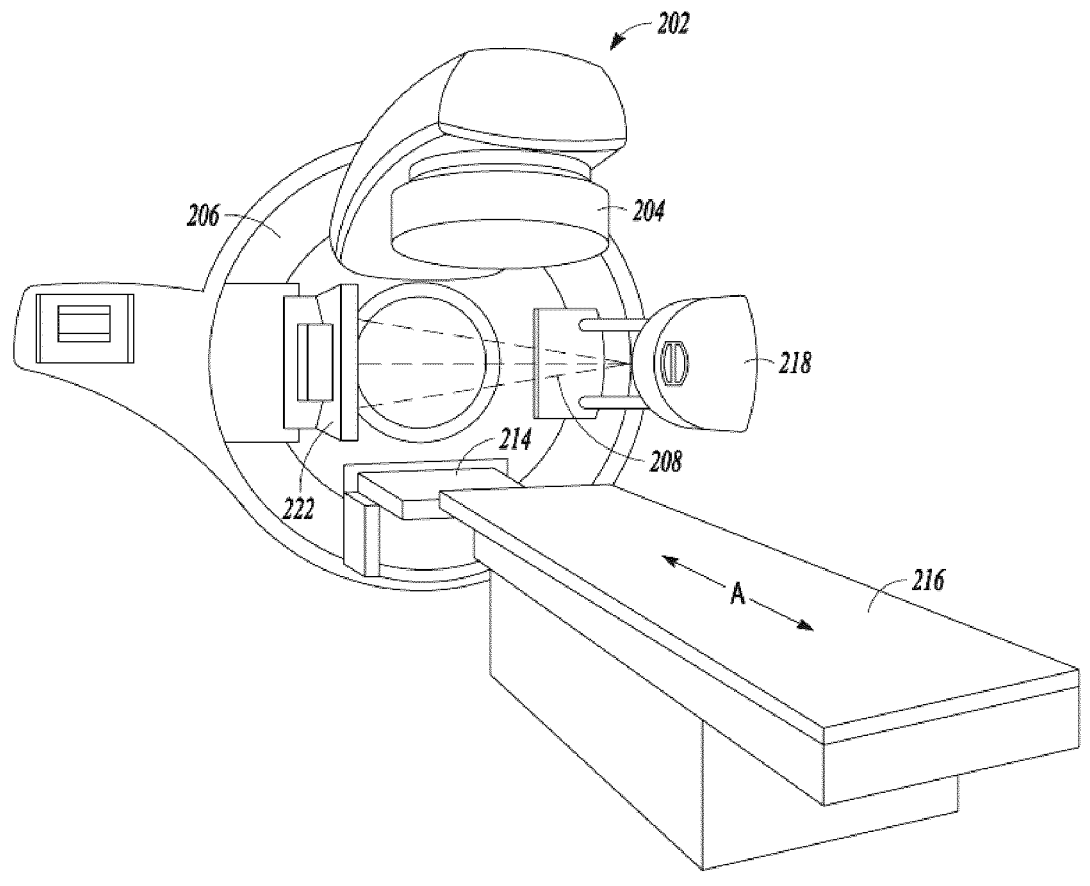
FIG. 2B illustrates an example system including a combined radiation therapy system and an imaging system, such as a cone beam computed tomography (CBCT) imaging system, according to some embodiments of the present disclosure.

FIG. 2B illustrates an example radiation therapy device 202 that may include a combined linac and an imaging system, such as can include a CT imaging system. The radiation therapy device 202 can include an MLC (not shown). The CT imaging system can include an imaging X-ray source 218, such as providing X-ray energy in a kiloelectron-Volt (keV) energy range. The imaging X-ray source 218 can provide a fan-shaped and/or a conical beam 208 directed to an imaging detector 222, such as a flat panel detector. The radiation therapy device 202 can be similar to the system described in relation to FIG. 2A, such as including a radiation therapy output 204, a gantry 206, a couch 216, and another imaging detector 214 (such as a flat panel detector). The X-ray source 218 can provide a comparatively lower-energy X-ray diagnostic beam, for imaging.

In the illustrative embodiment of FIG. 2B, the radiation therapy output 204 and the X-ray source 218 can be mounted on the same rotating gantry 206, rotationally separated from each other by 90 degrees. In another embodiment, two or more X-ray sources can be mounted along the circumference of the gantry 206, such as each having its own detector arrangement to provide multiple angles of diagnostic imaging concurrently. Similarly, multiple radiation therapy outputs 204 can be provided.

Figure 3:
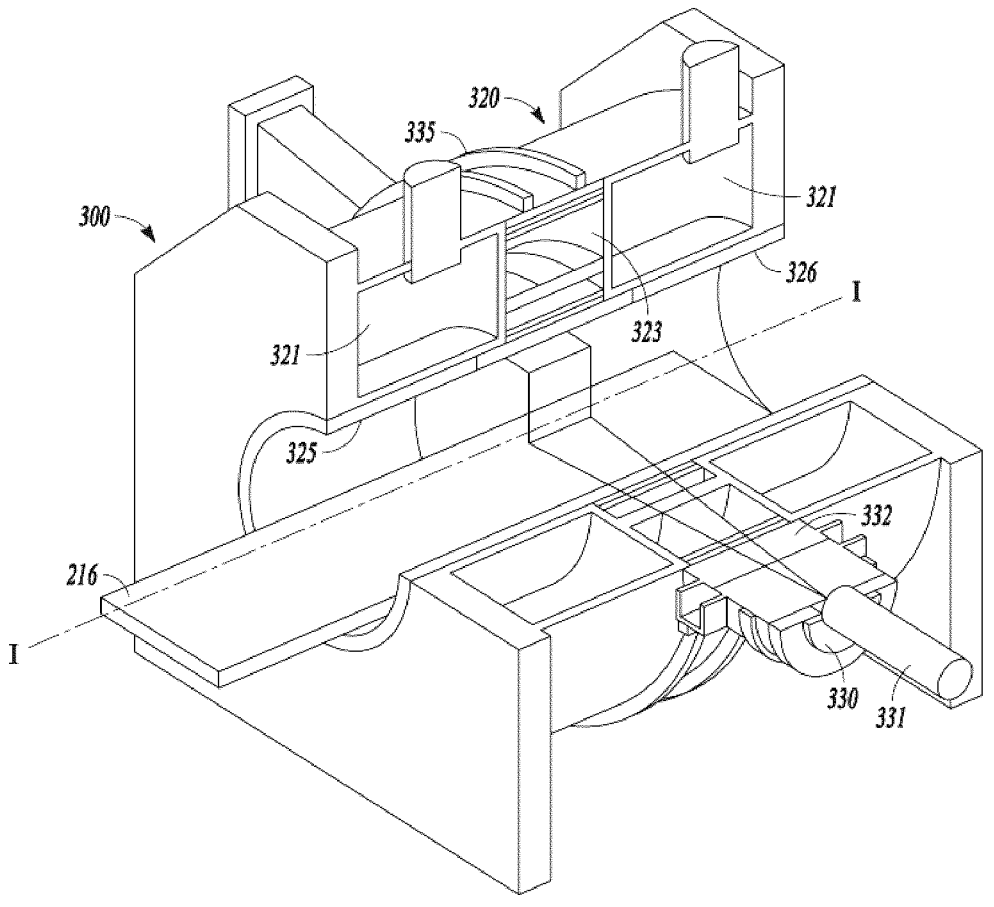
FIG. 3 illustrates a partially cut-away view of an example system including a combined radiation therapy system and an imaging system, such as a nuclear MR imaging (MRI) system, according to some embodiments of the present disclosure.
Figure 4:
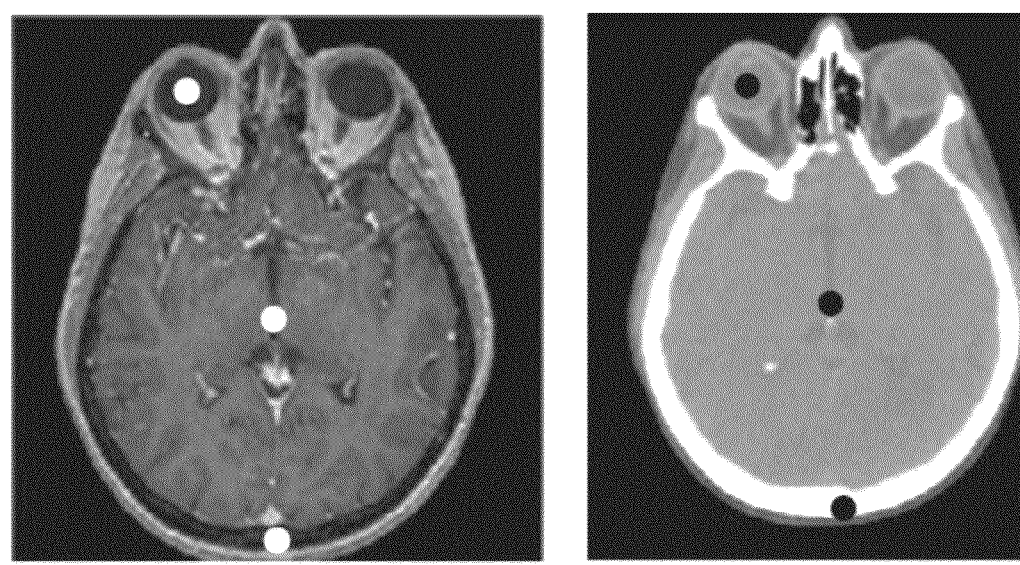
FIGS. 4A and 4B are images depicting differences between an example MRI image and a corresponding CT image, respectively, according to some embodiments of the present disclosure.

FIG. 3 depicts an example radiation therapy system 300 that can include combining a radiation therapy device 202 and an imaging system, such as a nuclear MR imaging system (e.g., known in the art as an MR-linac) consistent with the disclosed embodiments. As shown, system 300 may include a couch 216, an image acquisition device 320, and a radiation delivery device 330. System 300 delivers radiation therapy to a patient in accordance with a radiotherapy treatment plan. In some embodiments, image acquisition device 320 may correspond to image acquisition device 132 in FIG. 1 that may acquire origin images of a first imaging modality (e.g., MRI image shown in FIG. 4A) or destination images of a second imaging modality (e.g., CT image shown in FIG. 4B).

Couch 216 may support a patient (not shown) during a treatment session. In some implementations, couch 216 may move along a horizontal translation axis (labelled "I"), such that couch 216 can move the patient resting on couch 216 into and/or out of system 300. Couch 216 may also rotate around a central vertical axis of rotation, transverse to the translation axis. To allow such movement or rotation, couch 216 may have motors (not shown) enabling the couch 216 to move in various directions and to rotate along various axes. A controller (not shown) may control these movements or rotations in order to properly position the patient according to a treatment plan.

In some embodiments, image acquisition device 320 may include an MRI machine used to acquire 2D or 3D MRI images of the patient before, during, and/or after a treatment session. Image acquisition device 320 may include a magnet 321 for generating a primary magnetic field for magnetic resonance imaging. The magnetic field lines generated by operation of magnet 321 may run substantially parallel to the central translation axis I. Magnet 321 may include one or more coils with an axis that runs parallel to the translation axis I. In some embodiments, the one or more coils in magnet 321 may be spaced such that a central window 323 of magnet 321 is free of coils. In other embodiments, the coils in magnet 321 may be thin enough or of a reduced density such that they are substantially transparent to radiation of the wavelength generated by radiotherapy device 330. Image acquisition device 320 may also include one or more shielding coils, which may generate a magnetic field outside magnet 321 of approximately equal magnitude and opposite polarity in order to cancel or reduce any magnetic field outside of magnet 321. As described below, radiation source 331 of radiotherapy device 330 may be positioned in the region where the magnetic field is cancelled, at least to a first order, or reduced.

Image acquisition device 320 may also include two gradient coils 325 and 326, which may generate a gradient magnetic field that is superposed on the primary magnetic field. Coils 325 and 326 may generate a gradient in the resultant magnetic field that allows spatial encoding of the protons so that their position can be determined. Gradient coils 325 and 326 may be positioned around a common central axis with the magnet 321 and may be displaced along that central axis. The displacement may create a gap, or window, between coils 325 and 326. In embodiments where magnet 321 can also include a central window 323 between coils 325 and 326, the two windows may be aligned with each other.

In some embodiments, image acquisition device 320 may be an imaging device other than an MRI, such as an X-ray, a CT, a CBCT, a spiral CT, a PET, a SPECT, an optical tomography, a fluorescence imaging, ultrasound imaging, radiotherapy portal imaging device, or the like. As would be recognized by one of ordinary skill in the art, the above description of image acquisition device 320 concerns certain embodiments and is not intended to be limiting.

Figure 5:
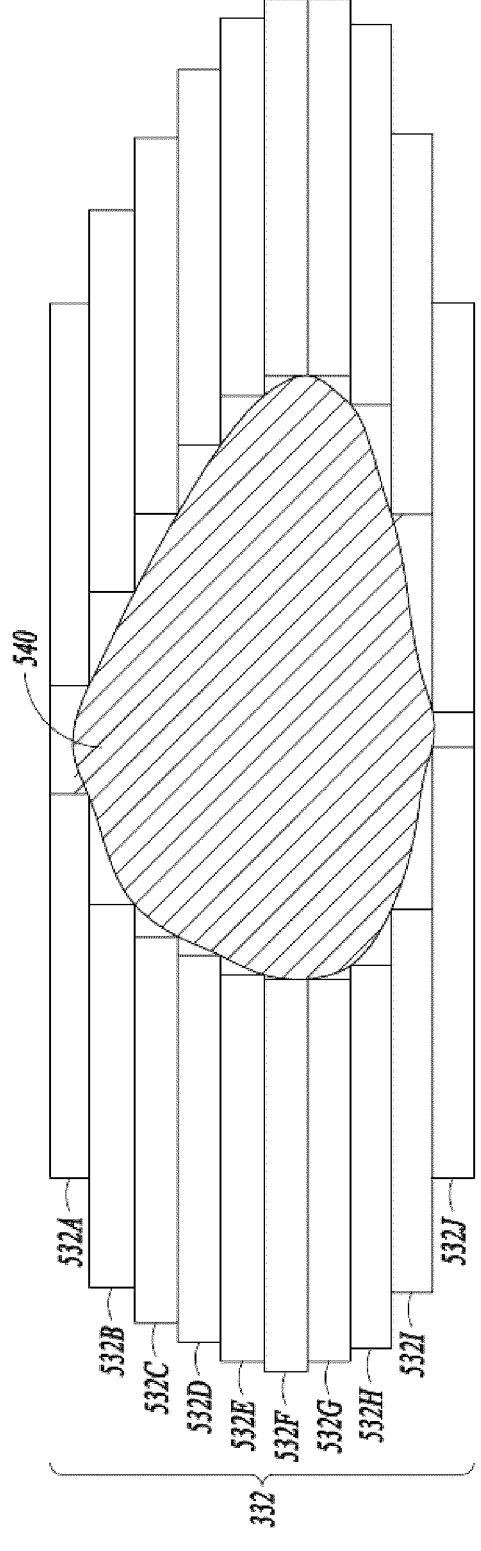
FIG. 5 illustrates an example collimator configuration for shaping, directing, or modulating an intensity of a radiation therapy beam, according to some embodiments of the present disclosure.

Radiotherapy device 330 may include the radiation source 331, such as an X-ray source or a linac, and an MLC 332 (shown below in FIG. 5). Radiotherapy device 330 may be mounted on a chassis 335. One or more chassis motors (not shown) may rotate chassis 335 around couch 216 when couch 216 is inserted into the treatment area. In an embodiment, chassis 335 may be continuously rotatable around couch 216, when couch 216 is inserted into the treatment area. Chassis 335 may also have an attached radiation detector (not shown), preferably located opposite to radiation source 331 and with the rotational axis of chassis 335 positioned between radiation source 331 and the detector. Further, device 330 may include control circuitry (not shown) used to control, for example, one or more of couch 216, image acquisition device 320, and radiotherapy device 330. The control circuitry of radiotherapy device 330 may be integrated within system 300 or remote from it.

During a radiotherapy treatment session, a patient may be positioned on couch 216. System 300 may then move couch 216 into the treatment area defined by magnet 321, coils 325 and 326, and chassis 335. Control circuitry may then control radiation source 331, MLC 332, and the chassis motor(s) to deliver radiation to the patient through the window between coils 325 and 326 according to a radiotherapy treatment plan.

FIG. 2A, FIG. 2B, and FIG. 3 illustrate generally embodiments of a radiation therapy device configured to provide radiotherapy treatment to a patient, including a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another embodiment, the therapy output can be fixed, such as located in a region laterally separated from the patient, and a platform supporting the patient can be used to align a radiation therapy isocenter with a specified target locus within the patient.

As discussed above, radiation therapy devices described by FIG. 2A, FIG. 2B, and FIG. 3 include an MLC for shaping, directing, or modulating an intensity of a radiation therapy beam to the specified target locus within the patient. FIG. 5 illustrates an example MLC 332 that includes leaves 532A through 532J that can be automatically positioned to define an aperture approximating a tumor 540 cross section or projection. The leaves 532A through 532J permit modulation of the radiation therapy beam. The leaves 532A through 532J can be made of a material specified to attenuate or block the radiation beam in regions other than the aperture, in accordance with the radiation treatment plan. For example, the leaves 532A through 532J can include metallic plates, such as comprising tungsten, with a long axis of the plates oriented parallel to a beam direction and having ends oriented orthogonally to the beam direction (as shown in the plane of the illustration of FIG. 2A). A "state" of the MLC 332 can be adjusted adaptively during a course of radiation therapy treatment, such as to establish a therapy beam that better approximates a shape or location of the tumor 540 or another target locus. This is in comparison to using a static collimator configuration or as compared to using an MLC 332 configuration determined exclusively using an "offline" therapy planning technique. A radiation therapy technique using the MLC 332 to produce a specified radiation dose distribution to a tumor or to specific areas within a tumor can be referred to as IMRT.

Figure 6:
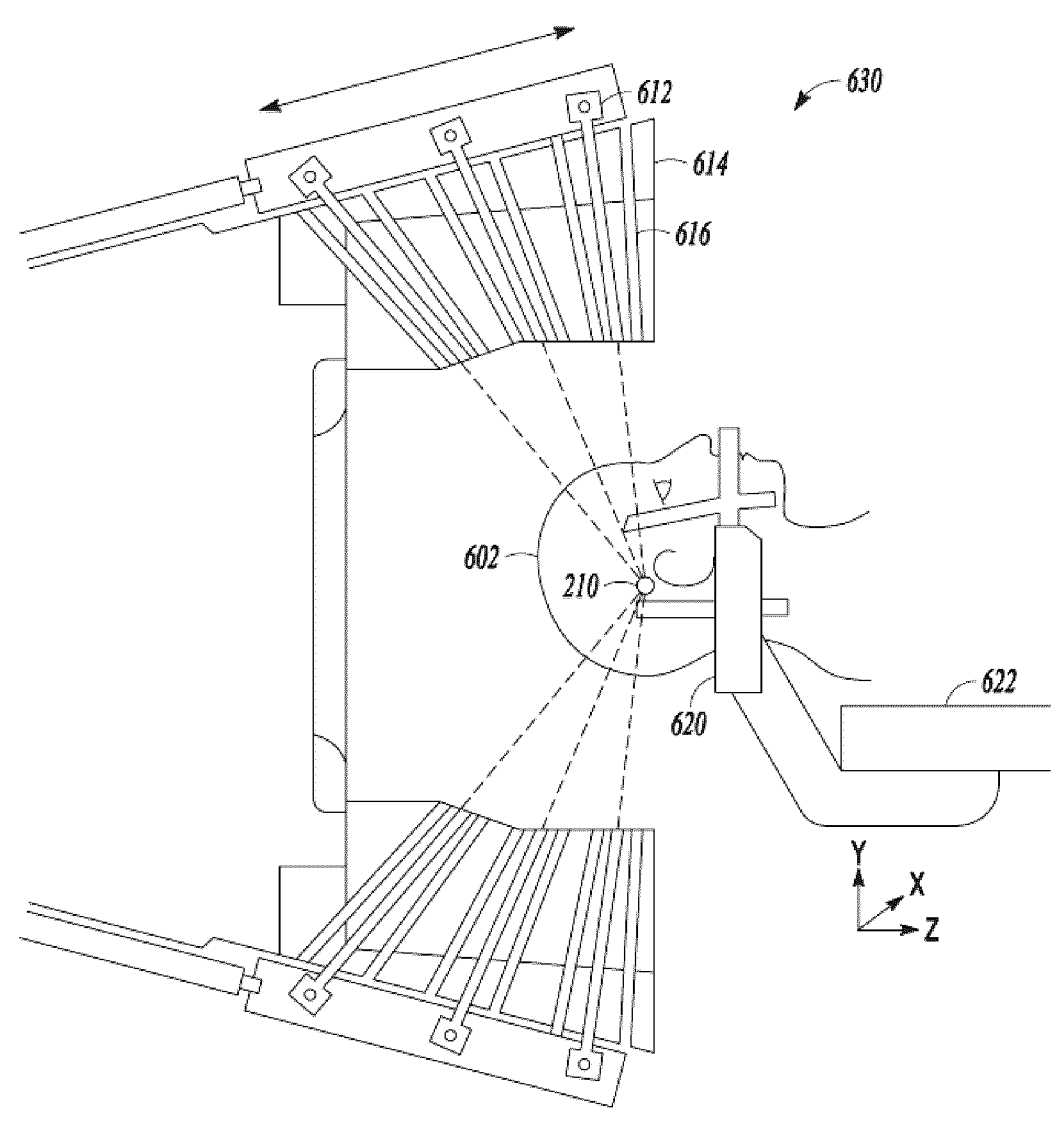
FIG. 6 illustrates an example Gamma Knife radiation therapy system, according to some embodiments of the present disclosure.

FIG. 6 illustrates an embodiment of another type of radiotherapy device 630 (e.g., a Leksell Gamma Knife), according to some embodiments of the present disclosure. As shown in FIG. 6, in a radiotherapy treatment session, a patient 602 may wear a coordinate frame 620 to keep stable the patient's body part (e.g., the head) undergoing surgery or radiotherapy. Coordinate frame 620 and a patient positioning system 622 may establish a spatial coordinate system, which may be used while imaging a patient or during radiation surgery. Radiotherapy device 630 may include a protective housing 614 to enclose a plurality of radiation sources 612. Radiation sources 612 may generate a plurality of radiation beams (e.g., beamlets) through beam channels 616. The plurality of radiation beams may be configured to focus on an isocenter 210 from different directions. While each individual radiation beam may have a relatively low intensity, isocenter 210 may receive a relatively high level of radiation when multiple doses from different radiation beams accumulate at isocenter 210. In certain embodiments, isocenter 210 may correspond to a target under surgery or treatment, such as a tumor.

Figure 7:
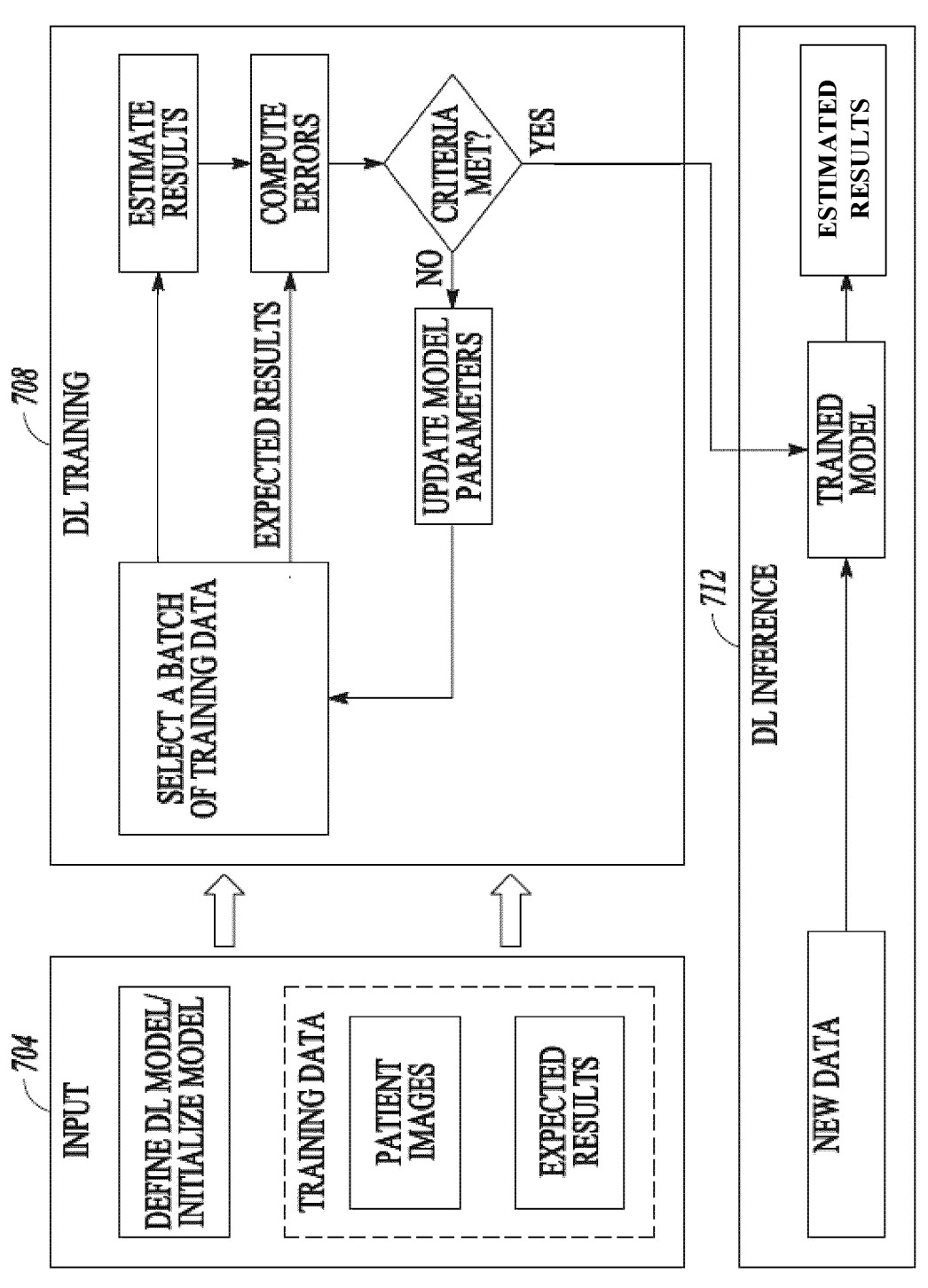
FIG. 7 illustrates an example flow diagram for deep learning, according to some embodiments of the present disclosure.

FIG. 7 illustrates an example flow diagram for deep learning, where a deep learning model (or a machine learning model), such as a deep convolutional neural network (DCNN), autoencoder neural network, or variational auto-encoder neural network, can be trained and used to generate predictions based on one or more training data, such as training medical images. After the DCNN is trained, the training data is analyzed to generate a distribution representation of the plurality of training data. The distribution representation is used to compute a distance between a given training data sample of the training data and the distribution representation. The distribution representation is also used to compute another distance between a new data sample and the distribution representation. Based on a difference or a deviation or level of similarity between the two distances, a quality factor can be computed that indicates how well the new data sample correlates with the training data. The quality factor can then be used to determine whether or not to apply the DCNN to the new data sample or to adjust or modify a weight of the output of the DCNN when applied to the new data sample. For example, if the quality factor is relatively high (or greater than a threshold), the DCNN can be applied to the new data sample with high confidence. In such cases, the output of the DCNN can be associated with a greater weight by a subsequent operation. If the quality factor is relatively low (or lower than a threshold), the DCNN can be applied to the new data sample with low confidence. In such cases, the output of the DCNN can be associated with a lower weight by a subsequent operation to reduce or avoid the impact of the output on other operations.

Inputs 704 can include a defined deep learning model (which can include one or more sub-networks or one or more individual and independent machine learning models) having an initial set of values and training data. The training data can include multiple training medical images of one or more patients and for different motion phases of periodic motion of a target region. The training data can be obtained in real time as a treatment fraction is being delivered or just prior to delivery of the treatment fraction.

The deep learning model can include one or more neural networks (referred to as sub-networks), such as a DCNN or autoencoder neural network. The deep learning network can be trained on the training data to establish a relationship between a given set of medical images representing different phases of periodic motion and feature vectors corresponding to the medical images. The feature vectors may include a low-dimensional feature space representation of the given set of medical images. In some cases, the DCNN can be trained to establish a relationship between the low-dimensional feature space representation and different groupings or clustering of motion phases. In this way, the DCNN can be applied to a set of medical images to generate the low-dimensional feature space representation of the medical images and to split the low-dimensional feature space representation into different groups that each corresponds to a different motion phase of periodic motion (e.g., a different breathing phase in a breathing cycle). In one embodiment, the deep learning network is trained in an end-to-end manner in which all of the sub-networks are trained simultaneously by being applied to a same set or batch of training data and minimizing a set of cost functions. In another embodiment, one or more of the sub-networks of the DCNN are trained separately and independently in sequence by minimizing a set of cost functions associated with each particular sub-network.

The training data can include medical images of the known patients or medical images of a single patient that can include images of an anatomy, CT images, PET images, or MRI images. The plurality of images can be collected from a magnetic resonance (MR) scanner, an ultrasound scanner, a kV image scanner, or an X-ray imaging device or any other imaging device or combination of imaging devices. When trained, the deep learning network can produce an estimate of a set of feature vectors of a new medical image. The expected results can include the training data itself.

During training of deep learning (DL) model 708, a batch of training data can be selected from the training data of known patients or of a patient undergoing radiotherapy. An encoder portion of the DL model 708 (e.g., the autoencoder neural network) is applied to the batch of training data to generate a plurality of feature vectors. A decoder portion of the DL model 708 (e.g., the autoencoder neural network) is applied to the plurality of feature vectors to generate reconstructed training data. A deviation is computed based on a comparison of the training data, and the reconstructed training data and parameters of the DL model 708 (e.g., the neural network autoencoder) are updated based on the computed deviation.

The errors or result of computing the loss function can be used during a procedure called backpropagation to update the parameters of the deep learning network (e.g., layer node weights and biases of each or of certain sub-networks of the model 708), in order to reduce or minimize errors during subsequent trials. The errors or result of computing the loss function can be compared to predetermined criteria, such as proceeding to a sustained minimum for a specified number of training iterations. If the errors or result of computing the loss function do not satisfy the predetermined criteria, then model parameters of the deep learning model 708 can be updated using backpropagation, and another batch of training data can be selected from the other sets of training data (of the same patient or other patients) and expected results for another iteration of deep learning model training. If the errors or result of computing the loss function satisfy the predetermined criteria, then the training can be ended, and the trained model 708 can then be used during a deep learning testing or inference stage 712 to generate feature vectors for subsequently received medical images.

After updating the parameters of the DCNN, the iteration index can be incremented by a value of one. The iteration index can correspond to a number of times that the parameters of the DCNN have been updated. Stopping criteria can be computed, and if the stopping criteria are satisfied, then the DCNN model can be saved in a memory, such as a memory device, and the training can be halted. If the stopping criteria are not satisfied, then the training can continue by obtaining another batch of training data from the same training subject or another training subject. In an embodiment, the stopping criteria can include a value of the iteration index (e.g., the stopping criteria can include whether the iteration index is greater than or equal to a determined maximum number of iterations). The steps recited above for training the DL model 708 can be repeated for each set or batch of training data associated with the same or different patient and/or region of interest.

After the DL model 708 is trained, before the DL model 708 is applied to a new medical image (data sample) to generate a set of feature vectors for the new image, a quality factor can be generated, as discussed above, to represent how similar the new data sample is to the training data used to train the DL model 708. If the quality factor exceeds a threshold, the DL model 708 can be applied to the new data sample to generate a prediction. If the quality factor is lower than the threshold, the DL model 708 can be skipped or the output of the DL model 708 resulting from application of the DL model 708 to the new data sample can be associated with a relatively low weight.

Figure 8:
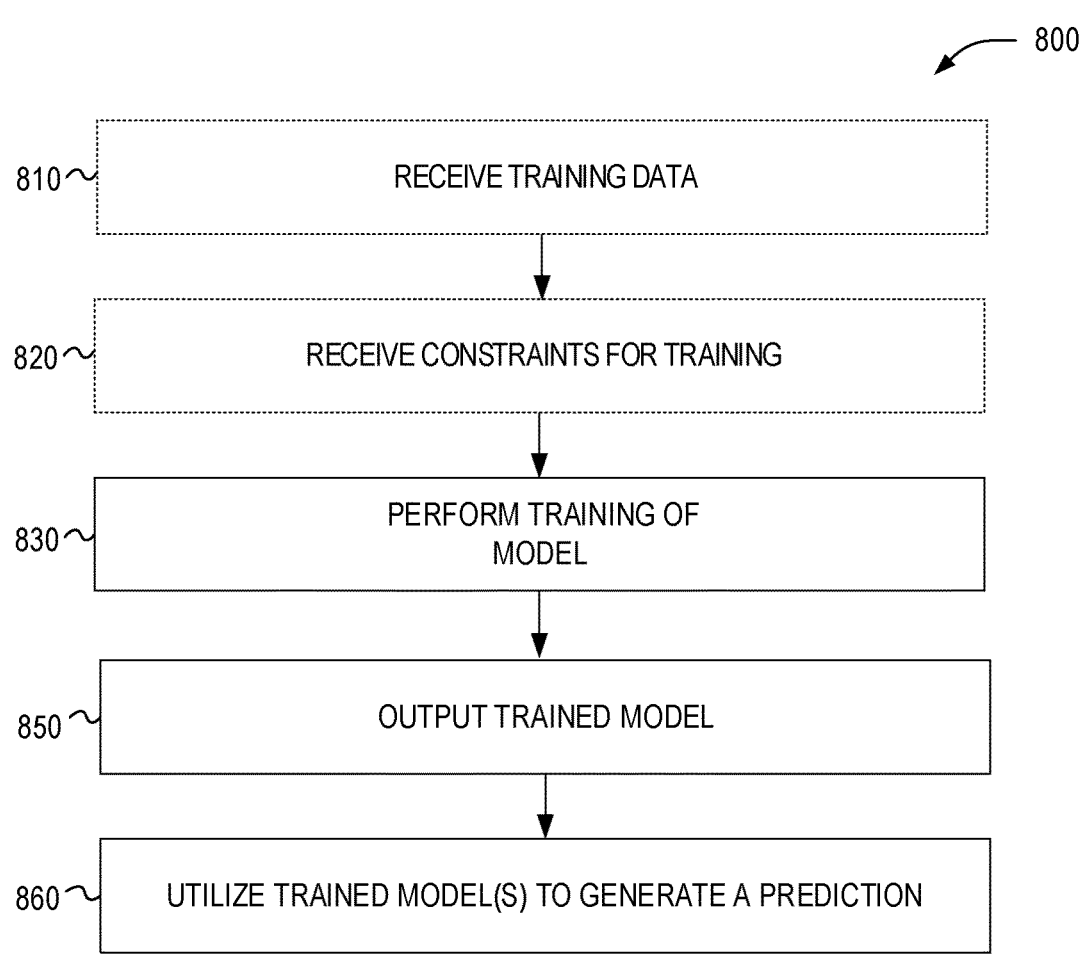
FIG. 8 illustrates an example data flow for training and use of a machine learning model, according to some embodiments of the present disclosure.

FIG. 8 is a flowchart illustrating example operations of the image processing device 112 in performing process 800, according to example embodiments. The process 800 may be embodied in computer-readable instructions for execution by one or more processors such that the operations of the process 800 may be performed in part or in whole by the functional components of the image processing device 112: accordingly, the process 800 is described below by way of example with reference thereto. However, in other embodiments, at least some of the operations of the process 800 may be deployed on various other hardware configurations. The process 800 is therefore not intended to be limited to the image processing device 112 and can be implemented in whole, or in part, by any other component. Some or all of the operations of process 800 can be in parallel, out of order, or entirely omitted.

At operation 810, image processing device 112 receives training data. For example, image processing device 112 receives training data, which may include paired training data sets (e.g., input-output training pairs).

At operation 820, image processing device 112 receives one or more cost functions for training the model.

At operation 830, image processing device 112 performs training of the model based on the received training data and one or more cost functions.

At operation 850, image processing device 112 outputs the trained model.

At operation 860, image processing device 112 utilizes the trained model to generate a prediction.

FIG. 9 is a flowchart illustrating example operations of the image processing device 112 in performing process 900, according to example embodiments. The process 900 may be embodied in computer-readable instructions for execution by one or more processors such that the operations of the process 900 may be performed in part or in whole by the functional components of the image processing device 112: accordingly, the process 900 is described below by way of example with reference thereto. However, in other embodiments, at least some of the operations of the process 900 may be deployed on various other hardware configurations. The process 900 is therefore not intended to be limited to the image processing device 112 and can be implemented in whole, or in part, by any other component. Some or all of the operations of process 900 can be in parallel, out of order, or entirely omitted.

At operation 910, image processing device 112 receives a plurality of training data used to train a machine learning technique, as discussed above.

At operation 920, image processing device 112 applies a model to the plurality of training data to generate a distribution representation of the plurality of training data, as discussed above.

At operation 930, image processing device 112 computes a first distance between a given training data in the plurality of training data and the distribution representation, as discussed above.

At operation 940, image processing device 112 computes a second distance between a new data sample and the distribution representation, as discussed above.

At operation 950, image processing device 112 computes a quality factor indicating a measure of similarity between a new data sample and the plurality of data as a function of the first distance and the second distance, as discussed above.

Figure 10:
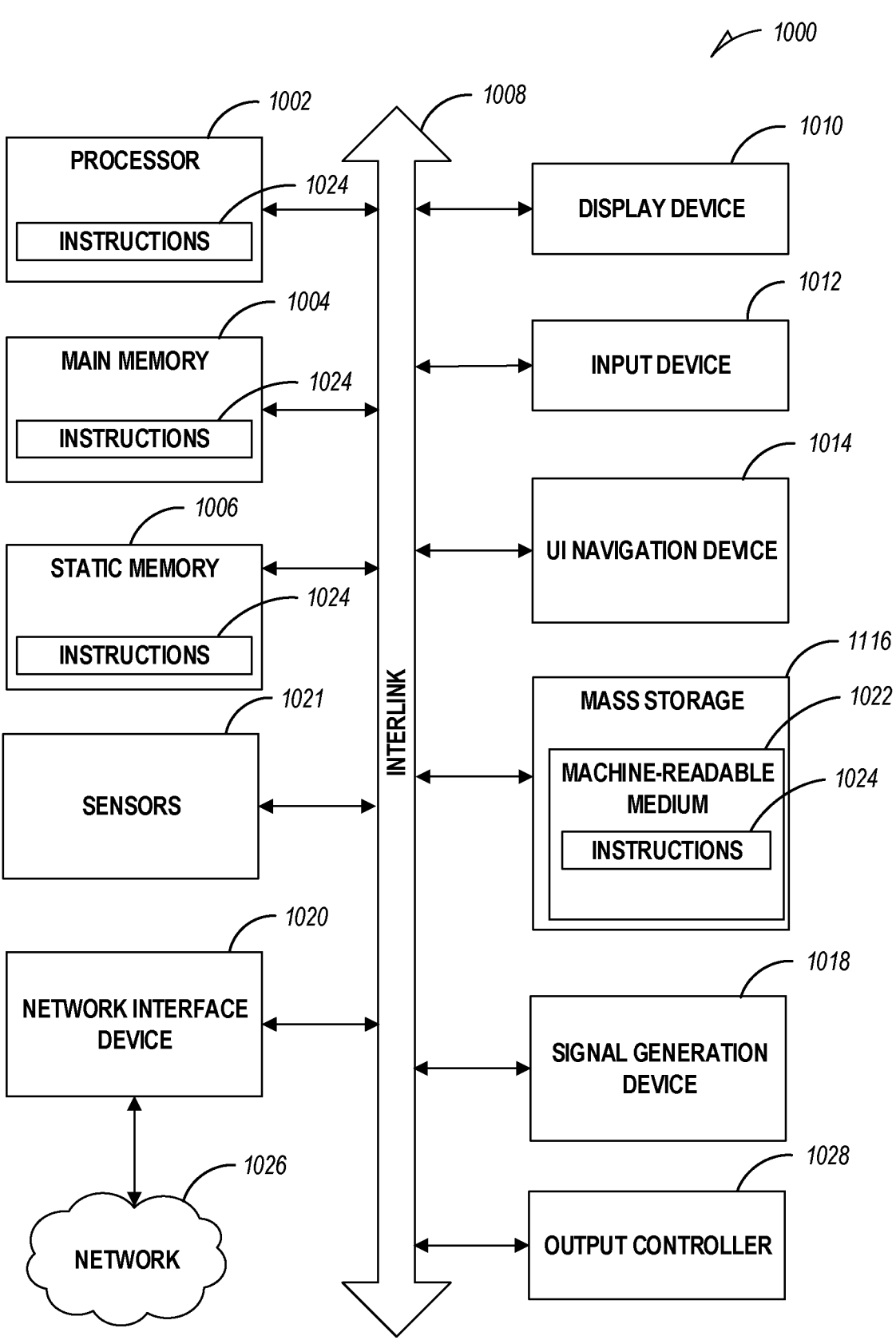
FIG. 10 illustrates an example block diagram of a machine on which one or more of the methods as discussed herein can be implemented.

FIG. 10 illustrates a block diagram of an embodiment of a machine 1000 on which one or more of the methods as discussed herein can be implemented. In one or more embodiments, one or more items of the image processing device 112 can be implemented by the machine 1000. In alternative embodiments, the machine 1000 operates as a standalone device or may be connected (e.g., networked) to other machines. In one or more embodiments, the image processing device 112 can include one or more of the items of the machine 1000. In a networked deployment, the machine 1000 may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example machine 1000 includes processor 1002 (e.g., a CPU, a GPU, an ASIC, circuitry, such as one or more transistors, resistors, capacitors, inductors, diodes, logic gates, multiplexers, buffers, modulators, demodulators, radios (e.g., transmit or receive radios or transceivers), sensors 1021 (e.g., a transducer that converts one form of energy (e.g., light, heat, electrical, mechanical, or other energy) to another form of energy), or the like, or a combination thereof), a main memory 1004 and a static memory 1006, which communicate with each other via a bus 1008. The machine 1000 (e.g., computer system) may further include a video display unit 1010 (e.g., a liquid crystal display (LCD) or a cathode ray tube (CRT)). The machine 1000 also includes an alphanumeric input device 1012 (e.g., a keyboard), a user interface (UI) navigation device 1014 (e.g., a mouse), a disk drive or mass storage unit 1116, a signal generation device 1018 (e.g., a speaker), and a network interface device 1020.

The disk drive or mass storage unit 1016 includes a machine-readable medium 1022 on which is stored one or more sets of instructions and data structures (e.g., software) 1024 embodying or utilized by any one or more of the methodologies or functions described herein. The instructions 1024 may also reside, completely or at least partially, within the main memory 1004 and/or within the processor 1002 during execution thereof by the machine 1000, the main memory 1004 and the processor 1002 also constituting machine-readable media.

The machine 1000 as illustrated includes an output controller 1028. The output controller 1028 manages data flow to/from the machine 1000. The output controller 1028 is sometimes called a device controller, with software that directly interacts with the output controller 1028 being called a device driver.

While the machine-readable medium 1022 is shown in an embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present disclosure, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), EEPROM, and flash memory devices; magnetic disks such as internal hard disks and removable disks; magneto-optical disks; and CD-ROM and DVD-ROM disks.

The instructions 1024 may further be transmitted or received over a communications network 1026 using a transmission medium. The instructions 1024 may be transmitted using the network interface device 1020 and any one of a number of well-known transfer protocols (e.g., HTTP). Examples of communication networks include a LAN, a WAN, the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

As used herein, "communicatively coupled between" means that the entities on either of the coupling must communicate through an item therebetween and that those entities cannot communicate with each other without communicating through the item.

Additional Notes

The above detailed description includes references to the accompanying drawings, which form a part of the detailed description. The drawings show, by way of illustration but not by way of limitation, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document: for irreconcilable inconsistencies, the usage in this document controls.

In this document, the terms "a," "an," "the," and "said" are used when introducing elements of aspects of the disclosure or in the embodiments thereof, as is common in patent documents, to include one or more than one of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that elements after such a term (e.g., comprising, including, having) in a claim are still deemed to fall within the scope of that claim. Moreover, in the following claims, the terms "first," "second," and "third," and so forth, are used merely as labels, and are not intended to impose numerical requirements on their objects.

Embodiments of the disclosure may be implemented with computer-executable instructions. The computer-executable instructions (e.g., software code) may be organized into one or more computer-executable components or modules. Aspects of the disclosure may be implemented with any number and organization of such components or modules. For example, aspects of the disclosure are not limited to the specific computer-executable instructions or the specific components or modules illustrated in the figures and described herein. Other embodiments of the disclosure may include different computer-executable instructions or components having more or less functionality than illustrated and described herein.

Method examples (e.g., operations and functions) described herein can be machine or computer-implemented at least in part (e.g., implemented as software code or instructions). Some examples can include a computer-readable medium or machine-readable medium encoded with instructions operable to configure an electronic device to perform methods as described in the above examples. An implementation of such methods can include software code, such as microcode, assembly language code, a higher-level language code, or the like (e.g., "source code"). Such software code can include computer readable instructions for performing various methods (e.g., "object" or "executable code"). The software code may form portions of computer program products. Software implementations of the embodiments described herein may be provided via an article of manufacture with the code or instructions stored thereon, or via a method of operating a communication interface to send data via a communication interface (e.g., wirelessly, over the internet, via satellite communications, and the like).

Further, the software code may be tangibly stored on one or more volatile or non-volatile computer-readable storage media during execution or at other times. These computer-readable storage media may include any mechanism that stores information in a form accessible by a machine (e.g., computing device, electronic system, and the like), such as, but not limited to, floppy disks, hard disks, removable magnetic disks, any form of magnetic disk storage media, CD-ROMS, magnetic-optical disks, removable optical disks (e.g., compact disks and digital video disks), flash memory devices, magnetic cassettes, memory cards or sticks (e.g., secure digital cards), RAMs (e.g., CMOS RAM and the like), recordable/non-recordable media (e.g., ROMs), EPROMS, EEPROMS, or any type of media suitable for storing electronic instructions, and the like. Such computer-readable storage medium may be coupled to a computer system bus to be accessible by the processor and other parts of the OIS.

In an embodiment, the computer-readable storage medium may have encoded a data structure for a treatment plan, wherein the treatment plan may be adaptive. The data structure for the computer-readable storage medium may be at least one of a Digital Imaging and Communications in Medicine (DICOM) format, an extended DICOM format, an XML format, and the like. DICOM is an international communications standard that defines the format used to transfer medical image-related data between various types of medical equipment. DICOM RT refers to the communication standards that are specific to radiation therapy.

In various embodiments of the disclosure, the method of creating a component or module can be implemented in software, hardware, or a combination thereof. The methods provided by various embodiments of the present disclosure, for example, can be implemented in software by using standard programming languages such as, for example, Compute Unified Device Architecture (CUDA), C, C++, Java, Python, and the like: and using standard machine learning/deep learning library (or API), such as tensorflow, torch and the like: and combinations thereof. As used herein, the terms "software" and "firmware" are interchangeable, and include any computer program stored in memory for execution by a computer.

A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may comprise a general-purpose computer selectively activated or reconfigured by a computer program stored in the computer. The order of execution or performance of the operations in embodiments of the disclosure illustrated and described herein is not essential, unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

In view of the above, it will be seen that the several objects of the disclosure are achieved, and other advantageous results attained. Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are example embodiments. Many other embodiments will be apparent to those of skill in the art upon reviewing the above description. The scope of the disclosure should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the disclosure should be determined with reference to the appended claims, along with the full scope of equivalents to which such claims are entitled. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

What is claimed is:

1. A system comprising:

a memory; and one or more processors that, when executing instructions stored in the memory, are configured to perform operations comprising:

receiving a plurality of training data used to train a machine learning technique;

applying a model to the plurality of training data to generate a distribution representation of the plurality of training data;

determining that the plurality of training data correspond to periodic motion;

in response to determining that the plurality of training data correspond to periodic motion, clustering the plurality of training data into a plurality of clusters each representative of an anatomic motion state;

computing a first distance between a given training data in the plurality of training data and the distribution representation;

computing a second distance between a new data sample and the distribution representation based on a given one of the plurality of clusters;

computing a quality factor indicating a measure of similarity between a new data sample and the plurality of training data as a function of the first distance and the second distance;

comparing the quality factor to a threshold value; and in response to determining that the quality factor exceeds the threshold value, increasing a confidence value associated with a result of applying the machine learning technique to the new data sample.

2. The system of claim 1, wherein the quality factor is indicative of a confidence level of applying the machine learning technique to the new data sample.

3. The system of claim 1, wherein the operations further comprise determining pixel intensity values for a plurality of training medical images.

4. The system of claim 3, wherein applying the model comprises:

generating a Principal Component Analysis (PCA) representation of the plurality of training medical images based on the pixel intensity values.

5. The system of claim 4, wherein the operations further comprise:

applying a threshold to the PCA representation of the plurality of training medical images to retain a portion of a plurality of components of the PCA representation; and projecting the plurality of training medical images to the portion of the plurality of components of the PCA representation.

6. The system of claim 5, wherein the operations further comprise:

computing a training probability of a distribution of the plurality of components of the PCA representation for each of the plurality of training medical images;

computing a new probability of a distribution associated with the new data sample relative to the plurality of components of the PCA representation; and comparing the new probability to the training probability of the distribution to generate the quality factor.

7. The system of claim 5, wherein the operations further comprise:

computing a plurality of distances by computing a Mahalanobis distance between each of the plurality of training medical images and the portion of the plurality of components of the PCA representation to generate a distribution of distances.

8. The system of claim 7, wherein the operations further comprise:

extracting a given percentile distance from the plurality of distances as the first distance;

normalizing the second distance by the given percentile distance; and comparing the normalized second distance to a threshold to generate the quality factor.

9. The system of claim 1, wherein the operations further comprise computing a plurality of distances for each of the plurality of clusters.

10. The system of claim 9, wherein the operations further comprise:

comparing the second distance to the plurality of distances;

identifying a cluster of the plurality of clusters associated with a minimum distance that results from comparing the second distance to the plurality of distances; and computing the quality factor as a function of the first distance and the minimum distance.

11. The system of claim 1, wherein the operations further comprise:

determining pixel intensity values for a plurality of training medical images; and generating, for each of the plurality of clusters, a Principal Component Analysis (PCA) representation of the plurality of training medical images based on the pixel intensity values.

12. The system of claim 1, wherein the operations further comprise:

registering the plurality of training data based on a motion template to generate a motion registered training image set;

applying the model to the motion registered training image set to generate a registered image distribution representation of the motion registered training image set; and registering the new data sample based on the motion template to generate a registered new data sample, wherein the second distance is computed based on a deviation between the registered new data sample and the registered image distribution representation.

13. The system of claim 1, wherein the training data comprises a plurality of training medical images including at least one of a cine image, a magnetic resonance (MR) image, an ultrasound image, a kV image, or an x-ray image.

14. A method comprising:

receiving a plurality of training data used to train a machine learning technique;

applying a model to the plurality of training data to generate a distribution representation of the plurality of training data;

determining that the plurality of training data correspond to periodic motion;

in response to determining that the plurality of training data correspond to periodic motion, clustering the plurality of training data into a plurality of clusters each representative of an anatomic motion state;

computing a first distance between a given training data in the plurality of training data and the distribution representation;

computing a second distance between a new data sample and the distribution representation based on a given one of the plurality of clusters;

computing a quality factor indicating a measure of similarity between a new data sample and the plurality of training data as a function of the first distance and the second distance;

comparing the quality factor to a threshold value; and in response to determining that the quality factor exceeds the threshold value, increasing a confidence value associated with a result of applying the machine learning technique to the new data sample.

15. The method of claim 14, wherein the quality factor is indicative of a confidence level of applying the machine learning technique to the new data sample.

16. The method of claim 14, further comprising determining pixel intensity values for a plurality of training medical images.

17. The method of claim 16, wherein applying the model comprises:

generating a Principal Component Analysis (PCA) representation of the plurality of training medical images based on the pixel intensity values.

18. The method of claim 17, further comprising:

applying a threshold to the PCA representation of the plurality of training medical images to retain a portion of a plurality of components of the PCA representation; and projecting the plurality of training medical images to the portion of the plurality of components of the PCA representation.

19. The method of claim 18, further comprising:

computing a training probability of a distribution of the plurality of components of the PCA representation for each of the plurality of training medical images;

computing a new probability of a distribution associated with the new data sample relative to the plurality of components of the PCA representation; and comparing the new probability to the training probability of the distribution to generate the quality factor.

20. The method of claim 18, further comprising:

computing a plurality of distances by computing a Mahalanobis distance between each of the plurality of training medical images and the portion of the plurality of components of the PCA representation to generate a distribution of distances.

21. The method of claim 20, further comprising:

extracting a given percentile distance from the plurality of distances as the first distance;

normalizing the second distance by the given percentile distance; and comparing the normalized second distance to a threshold to generate the quality factor.

22. The method of claim 14, further comprising computing a plurality of distances for each of the plurality of clusters.

23. The method of claim 22, further comprising:

comparing the second distance to the plurality of distances;

identifying a cluster of the plurality of clusters associated with a minimum distance that results from comparing the second distance to the plurality of distances; and computing the quality factor as a function of the first distance and the minimum distance.

24. The method of claim 14, further comprising:

determining pixel intensity values for a plurality of training medical images; and generating, for each of the plurality of clusters, a Principal Component Analysis (PCA) representation of the plurality of training medical images based on the pixel intensity values.

25. The method of claim 14, further comprising:

registering the plurality of training data based on a motion template to generate a motion registered training image set;

applying the model to the motion registered training image set to generate a registered image distribution representation of the motion registered training image set; and registering the new data sample based on the motion template to generate a registered new data sample, wherein the second distance is computed based on a deviation between the registered new data sample and the registered image distribution representation.

26. The method of claim 14, wherein the training data comprises a plurality of training medical images including at least one of a cine image, a magnetic resonance (MR) image, an ultrasound image, a kV image, or an x-ray image.

27. A non-transitory computer-readable medium comprising non-transitory computer-readable instructions for performing operations of claim 1.

* * * * *